United States Patent
Fang et al.

(10) Patent No.: US 11,498,961 B2
(45) Date of Patent: Nov. 15, 2022

(54) SOST ANTIBODY PHARMACEUTICAL COMPOSITION AND USES THEREOF

(71) Applicants: Jiangsu Hengrui Medicine Co., Ltd., Jiangsu (CN); Shanghai Hengrui Pharmaceutical Co., Ltd., Shanghai (CN)

(72) Inventors: Jingjing Fang, Shanghai (CN); Zhen Yan, Shanghai (CN); Xun Liu, Shanghai (CN)

(73) Assignees: Jiangsu Hengrui Medicine Co., Ltd., Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 216 days.

(21) Appl. No.: 16/632,596

(22) PCT Filed: Jul. 26, 2018

(86) PCT No.: PCT/CN2018/097165
§ 371 (c)(1),
(2) Date: Jan. 21, 2020

(87) PCT Pub. No.: WO2019/020069
PCT Pub. Date: Jan. 31, 2019

(65) Prior Publication Data
US 2020/0199209 A1    Jun. 25, 2020

(30) Foreign Application Priority Data
Jul. 27, 2017 (CN) .......................... 201710621754.2

(51) Int. Cl.
*A61K 39/395*  (2006.01)
*C07K 16/18*   (2006.01)
*A61K 9/08*    (2006.01)
*A61K 9/19*    (2006.01)

(52) U.S. Cl.
CPC ................ *C07K 16/18* (2013.01); *A61K 9/08* (2013.01); *A61K 9/19* (2013.01); *C07K 2317/24* (2013.01)

(58) Field of Classification Search
None
See application file for complete search history.

(56) References Cited

U.S. PATENT DOCUMENTS

| 10,449,250 B2 * | 10/2019 | Liu ........................ C07K 16/18 |
| 2010/0226928 A1 * | 9/2010 | Dani ........................ A61K 9/19 |
| | | 424/152.1 |

FOREIGN PATENT DOCUMENTS

| CN | 101646457 A | 2/2010 |
| CN | 101821291 A | 9/2010 |
| CN | 103435698 A | 12/2013 |
| WO | 03/073991 A2 | 9/2003 |
| WO | 2010/100200 A2 | 9/2010 |
| WO | 2012/028683 A1 | 3/2012 |
| WO | 2012/135035 A1 | 10/2012 |
| WO | 2016/145961 A1 | 9/2016 |

OTHER PUBLICATIONS

Int'l Search Report dated Oct. 18, 2018 in Int'l Application No. PCT/CN2018/097165.

* cited by examiner

*Primary Examiner* — Yunsoo Kim
(74) *Attorney, Agent, or Firm* — Ice Miller LLP

(57) ABSTRACT

A pharmaceutical composition containing an SOST antibody or an antigen-binding fragment thereof in an acetic acid-sodium acetate buffer solution is described. In addition, the pharmaceutical composition can also contain sugar, a nonionic surfactant or other excipients. After being stored for several months, the pharmaceutical composition exhibits good antibody stability.

14 Claims, No Drawings
Specification includes a Sequence Listing.

SOST ANTIBODY PHARMACEUTICAL COMPOSITION AND USES THEREOF

CROSS-REFERENCE TO RELATED APPLICATION

This application is a Section 371 of International Application No. PCT/CN2018/097165, filed Jul. 26, 2018, which was published in the Chinese language on Jan. 31, 2019, under International Publication No. WO 2019/020069 A1 which claims priority under 35 U.S.C. § 119(b) to Chinese Application No. 201710621754.2, filed Jul. 27, 2017, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 688452_I32US", creation date of Jan. 20, 2020, and having a size of about 36.4 kB. The sequence listing submitted via EFS-Web is part of the specification and is herein incorporated by reference in its entirety.

FIELD OF THE INVENTION

The present disclosure relates to the field of pharmaceutical preparations, in particular to a pharmaceutical composition comprising an anti-SOST antibody or antigen-binding fragment thereof, and use thereof as a medicament.

BACKGROUND OF THE INVENTION

Osteoporosis (OP), including postmenopausal Osteoporosis (PMO) and senile osteoporosis, is a systemic bone metabolism disorder that is characterized by low bone mass and degradation of bone microstructure, resulting in decreased bone strength, increased bone fragility, and increased risk of fracture. According to statistics, about 200 million people suffer from osteoporosis in the world, and the incidence has become one of the top seven most common and frequently occurring diseases. The prevalence rate of osteoporosis in Chinese females over 60 years old is as high as 60%, and the prevalence rate for males is 40-50%.

In addition to traditional measures, such as doing exercises, taking calcium and vitamin D, and publicizing knowledge about how to prevent bone fractures, the current medical treatment mainly focuses on reducing bone resorption for preventing bone fracture. The anti-bone resorption drugs include calcitonin, bisphosphonates, estrogen replacement agents and selective estrogen receptor modulators (SERMs), etc. The bisphosphonate bone resorption inhibitors can prevent further loss of bone, however, they fail to reconstruct bone loss. Further, these bone resorption inhibitors also inhibit osteogenesis while inhibiting bone resorption. Hormone drugs have a greater risk of causing venous thrombosis and cardiovascular diseases. More importantly, bone anabolic drugs, ideally, should not only improve bone mass, but also effectively improve the bone microstructure and promote osteogenesis. However, this is precisely what the existing anti-bone resorption drugs cannot achieve. In the past 15 years, various medical measures aiming at reducing the risk of fracture have been systematically investigated in clinical trials, and there is still a great need for effective drugs. So far, only parathyroid hormone (PTH) drugs have been proven to stimulate osteogenesis. However, PTH drugs have many clear disadvantages. For example, their effect on remodeling bones is not long lasting, they have little effect on repairing bone fracture, they may require daily percutaneous injections for up to a year or more, they can only be administered at low-dose, they are expensive and cannot be continuously used for more than two years, and their safety concerns revealed by the black-box warning by the FDA, the United States, and the like.

Sclerostin is proposed as a new biological target for drug development, with the theory that osteoporosis can be treated by regulating anabolism of osteoblasts. Such a target fills in gaps in the field of the treatment of osteoporosis by regulating bone metabolism.

Sclerostin is a glycoprotein secreted by the expression of the SOST gene, and its amino acid sequence is characterized by 190 residues and a loop domain containing cysteine. It has been shown that sclerostin is mainly expressed in bone cells, with very low expression in osteoblasts, cartilage, liver, kidney, bone marrow, heart, pancreas and other locations.

Studies have shown that sclerostin can regulate osteogenesis through inhibiting the Wnt signaling pathway by binding to low-density lipoprotein receptor LRP5/6. Presently, monoclonal antibody drugs against the target developed by several companies have entered into phase III or II clinical trials. The clinical data provided by three companies all demonstrated that the antibodies treated osteoporosis by regulating bone metabolism via the antibody target, and demonstrated that the treatments were safe and significantly potent. A clinical report for an anti-sclerostin antibody, Romosozumab, provided by Amgen and UCB, indicated that its safety and tolerance were both good, and that the bone density was significantly increased in treated bones compared to control. The drug has been advanced into clinical trial phase III. Another two monoclonal antibody drugs have been advanced into clinical trial phase II by Lilly and Novartis. These antibodies are indicated for the treatment of osteoporosis, bone damage/related osteopathy, etc. It is worth mentioning that some studies have shown that anti-sclerostin antibodies do not conflict with traditional bisphosphonates treatments, and these two drugs can be used in combination.

However, antibody drugs have large molecular weights, complex structures, and are easily degraded, polymerized, or undesirably chemically modified. In order to make antibodies suitable for administration, maintain stability and exert better effects after storage and during subsequent use, studies on stable formulations of antibody drugs are particularly important.

There are currently many companies developing pharmaceutical formulations comprising anti-SOST antibodies, for example, WO2016145961, WO2012028683, WO2012135035, and the like. However, with respect to new anti-SOST antibodies, there is still a need to develop pharmaceutical (formulation) compositions containing anti-SOST antibodies that are more suitable for administration.

SUMMARY OF THE INVENTION

The present disclosure provides a pharmaceutical composition, comprising an anti-SOST antibody or antigen biding fragment thereof, and a buffer, wherein the buffer is selected from the group consisting of acetate buffer, histidine buffer, phosphate buffer and succinate buffer, preferably acetate buffer, more preferably acetic acid-sodium acetate buffer.

In an alternative embodiment, in the pharmaceutical composition, the concentration of the anti-SOST antibody or antigen binding fragment thereof (i.e., the concentration of the SOST antibody or antigen-binding fragment thereof prepared in the buffer) is about 1 mg/ml to 120 mg/ml, preferably about 60 mg/ml to 120 mg/ml, further preferably about 80 mg/ml to 120 mg/ml, most preferably about 90 mg/ml to 110 mg/ml, further preferably 80 mg/ml to 100 mg/ml. Non-limiting embodiments of the concentration include 90 mg/ml, 91 mg/ml, 92 mg/ml, 93 mg/ml, 94 mg/ml, 95 mg/ml, 96 mg/ml, 97 mg/ml, 98 mg/ml, 99 mg/ml, 100 mg/ml, 101 mg/ml, 102 mg/ml, 103 mg/ml, 104 mg/ml, 105 mg/ml, 106 mg/ml, 107 mg/ml, 108 mg/ml, 109 mg/ml, 110 mg/ml, most preferably about 100 mg/ml.

In an alternative embodiment, the concentration of the buffer is about 5 mM to 30 mM, preferably about 10 mM to 20 mM. Non-limiting embodiments of the concentration of the buffer include 10 mM, 12 mM, 14 mM, 16 mM, 18 mM, 20 mM, most preferably 10 mM.

In an alternative embodiment, the pH value of the buffer in the pharmaceutical composition is about 4.8 to 5.5, preferably about 5.0 to 5.5. Non-limiting embodiments of the pH may be about 5.0, 5.1, 5.2, 5.3, 5.4, 5.5, most preferably about 5.0. After formulating the pharmaceutical composition with the buffer of the present disclosure, the final pH of the pharmaceutical composition is about 0.2-0.3 higher than the pH of the buffer. Thus, in an alternative embodiment, the pH of the pharmaceutical composition in the disclosure is about 4.8 to 5.5, preferably about 5.0 to 5.5. In non-limiting embodiments, the pH of the pharmaceutical composition may be about 5.0, 5.1, 5.2, 5.3, 5.4, 5.5, most preferably about 5.2 or 5.3.

Further, in an alternative embodiment, the pharmaceutical composition also comprises saccharide. The "saccharide" of the present disclosure encompasses the conventional composition $(CH_2O)_n$ and derivatives thereof, including monosaccharide, disaccharide, trisaccharide, polysaccharide, sugar alcohol, reducing sugar, non-reducing sugar and the like, which can be selected from the group consisting of glucose, sucrose, trehalose, lactose, fructose, maltose, dextran, glycerol, erythritol, arabitol, xylitol, sorbitol, mannitol, melibiose, melezitose, melitriose, mannotriose, stachyose, lactulose, maltulose, sorbitol, maltitol, lactitol, isomaltulose and the like. The saccharide is preferably non-reducing disaccharide, more preferably trehalose or sucrose.

In an alternative embodiment, the concentration of the saccharide in the pharmaceutical composition is about 40 mg/mL to 95 mg/mL, preferably about 60 mg/mL to 90 mg/mL. Non-limiting embodiments of the concentration of the saccharide include 60 mg/ml, 65 mg/ml, 70 mg/ml, 75 mg/ml, 80 mg/ml, 85 mg/ml, 90 mg/ml, more preferably 80 mg/ml.

In an alternative embodiment, the pharmaceutical composition also comprises a surfactant, which can be selected from the group consisting of polysorbate 20, polysorbate 80, poloxamer, Triton, sodium dodecyl sulfonate, sodium lauryl sulfonate, sodium octyl glycoside, lauryl-sulfobetaine, myristyl-sulfobetaine, linoleyl-sulfobetaine, stearyl-sulfobetaine, lauryl-sarcosine, myristyl-sarcosine, linoleyl-sarcosine, stearyl-sarcosine, linoleyl-betaine, myristyl-betaine, cetyl-betaine, lauryl amidopropyl-betaine, cocaramidopropyl-betaine, linoleamidopropyl-betaine, myristamidopropyl-betaine, palmitoylamidopropyl-betaine, isostearamidopropyl-betaine, myristamidopropyl-dimethylamine, palmitoylamidopropyl-dimethylamine, isostearamidopropyl-dimethylamine, sodium methyl cocoacyl, dissodium methyl oleyl-taurate, polyethylene glycol, polypropylene glycol, and copolymer of ethylene and propylene glycol, etc. The surfactant is preferably polysorbate 80 or polysorbate 20, more preferably polysorbate 80.

In an alternative embodiment, the concentration of the surfactant in the pharmaceutical composition is about 0.02 mg/ml to 0.8 mg/ml, preferably about 0.3 mg/ml to 0.6 mg/ml, non-limiting embodiment of the concentration of the surfactant includes 0.3 mg/ml, 0.35 mg/ml, 0.4 mg/ml, 0.45 mg/ml, 0.5 mg/ml, 0.55 mg/ml, 0.6 mg/ml, more preferably about 0.4 mg/ml.

In an alternative embodiment, the pharmaceutical composition further comprises a viscosity modifier. The viscosity modifier may be selected from the group consisting of calcium salt, sodium chloride, magnesium chloride and arginine hydrochloric acid, and is preferably calcium chloride or calcium acetate.

In an alternative embodiment, the concentration of the calcium salt in the pharmaceutical composition is preferably about 4.5 mM to 20 mM, preferably about 4.5 mM to 10 mM. Non-limiting examples include 4.5 mM, 5 mM, 5.5 mM, 6.0 mM, 6.5 mM, 7.0 mM, 7.5 mM, 8.0 mM, 8.5 mM, 9.0 mM, 9.5 mM, 10 mM, most preferably is about 0.4 mg/ml.

In an alternative embodiment, the pharmaceutical composition comprises:
(a) 1 mg/ml-120 mg/ml anti-SOST antibody or antigen binding fragment thereof;
(b) 5 mM-30 mM acetate buffer;
(c) 45 mg/mL-95 mg/mL trehalose;
(d) 0.02 mg/mL-0.8 mg/mL polysorbate 80; and
(e) 4.5 mM-20 mM calcium salt; preferably the pH of the pharmaceutical composition is about 4.8 to 5.5, more preferably is about 5.0 to 5.2.

In an alternative embodiment, the pharmaceutical composition comprises:
(a) 90 mg/ml-110 mg/ml anti-SOST antibody or antigen binding fragment thereof;
(b) 10 mM-20 mM acetate buffer;
(c) 60 mg/mL-90 mg/mL trehalose;
(d) 0.3 mg/mL-0.6 mg/mL polysorbate 80; and
(e) 4.5 mM-10 mM calcium salt; preferably the pH of the pharmaceutical composition is 5.0 to 5.2.

In an alternative embodiment, the pharmaceutical composition comprises:
(a) 100 mg/ml anti-SOST antibody or antigen binding fragment thereof;
(b) 10 mM acetate buffer;
(c) 80 mg/mL trehalose;
(d) 0.4 mg/mL polysorbate 80; and
(e) 4.5 mM calcium salt; preferably the pH of the pharmaceutical composition is 5.0, wherein the acetate buffer is acetic acid-sodium acetate buffer.

In an alternative embodiment, the pharmaceutical composition comprises:
(a) 80 mg/ml-100 mg/ml anti-SOST antibody or antigen binding fragment thereof; and
(b) 10 mM-20 mM acetate buffer, and the pH of the pharmaceutical composition is 5.0 to 5.2.

In an alternative embodiment, the pharmaceutical composition comprises:
(a) 100 mg/ml anti-SOST antibody or antigen binding fragment thereof;
(b) 10 mM acetic acid-sodium acetate buffer, pH 5.0;
(c) 80 mg/mL trehalose;
(d) 0.4 mg/mL polysorbate 80; and
(e) 4.5 mM calcium chloride.

In an alternative embodiment, the anti-SOST antibody or antigen binding fragment thereof present in the pharmaceutical composition comprises a HCDR1, HCDR2 and HCDR3 sequences as shown in SEQ ID NO: 3, SEQ ID NO: 9 and SEQ ID NO: 5, respectively; and a LCDR1, LCDR2 and LCDR3 as shown in SEQ ID NO: 6, SEQ ID NO: 7 and SEQ ID NO: 8, respectively.

In an alternative embodiment, the anti-SOST antibody or antigen binding fragment thereof comprises a heavy chain variable region having a sequence of SEQ ID NO: 10 and a light chain variable region having a sequence of SEQ ID NO: 13.

In an alternative embodiment, the anti-SOST antibody or antigen binding fragment thereof present in the pharmaceutical composition is selected from the group consisting of a murine antibody, a chimeric antibody, a humanized antibody, preferably is a humanized antibody.

In an alternative embodiment, the light chain amino acid sequence of the anti-SOST antibody present in the pharmaceutical composition has at least 85%, 86%, 87%, 88%, 89%, 90%, 91%, 92%, 93%, 94%, 95%, 96%, 97%, 98%, 99% or 100% sequence identity to the light chain amino acid sequence of Ab-5, the heavy chain amino acid sequence of the anti-SOST antibody has at least 85%, 86%, 87%, 88%, 89%, 90%, 91%, 92%, 93%, 94%, 95%, 96%, 97%, 98%, 99% or 100% sequence identity to the heavy chain amino acid sequence of Ab-5. The light chain sequence of antibody Ab-5 is shown in SEQ ID NO: 25, and the heavy chain sequence of antibody Ab-5 is shown in SEQ ID NO:22.

The present disclosure also provides a method of preparing a lyophilized formulation containing an anti-SOST antibody, comprising a step of freeze-drying the pharmaceutical composition described above.

In an alternative embodiment of the method of preparing a lyophilized formulation containing an anti-SOST antibody, the freeze-drying comprises sequentially pre-freezing, primary drying, and secondary drying. The pre-freezing is freezing from 5° C. to −40° C.−−50° C., most preferably to −45° C., regardless of the degree of vacuum. The temperature for the primary freeze-drying is −30° C. to 0° C., most preferably is −27° C.; the degree of vacuum is 0.05 mBar to 0.2 mBar, most preferably is 0.1 mBar. The temperature for the secondary drying is 20° C. to 30° C., most preferably is 25° C., the degree of vacuum is decreased from 0.05 mBar-0.2 mBar, most preferably 0.1 mBar, to 0.005 mBar-0.02 mBar, most preferably 0.01 mBar.

The present disclosure further provides a lyophilized formulation containing an anti-SOST antibody prepared by the method of preparing a lyophilized formulation containing an anti-SOST antibody as described above.

In some embodiments, the lyophilized formulation is stable at 2-8° C. for at least 3 months, at least 6 months, at least 12 months, at least 18 months, or at least 24 months. In some embodiments, the lyophilized formulation is stable at 40° C. for at least 7 days, at least 14 days or at least 28 days.

The present disclosure further provides a method of preparing a reconstituted solution comprising an anti-SOST antibody, comprising the step of reconstituting the lyophilized formulation as described above, wherein the solvent for reconstitution is selected from, but not limited to the group consisting of water for injection, physiological saline and glucose solution. Reconstitution according to the present disclosure means dissolving the lyophilized protein formulation in a diluent (which is selected from, but not limited to, the group consisting of water for injection, physiological saline and glucose solution) such that the protein is dispersed in the reconstituted preparation, i.e. a corresponding reconstituted solution can be obtained.

The present disclosure further provides a reconstituted solution containing an anti-SOST antibody prepared by the method of preparing a reconstituted solution comprising an anti-SOST antibody as described above.

In an alternative embodiment of the reconstituted solution containing an anti-SOST antibody, the concentration of the anti-SOST antibody and antigen binding fragment thereof is 80 mg/ml to 100 mg/ml; most preferably 100 mg/ml.

In an alternative embodiment of the reconstituted solution containing an anti-SOST antibody, the pH of the reconstituted solution is 4.8 to 5.5, preferably 5.3.

In an alternative embodiment, the reconstituted solution containing an anti-SOST antibody further comprises acetic acid-sodium acetate buffer, wherein the concentration of the acetic acid-sodium acetate buffer is 10 mM to 30 mM, preferably 10 mM.

In an alternative embodiment, the reconstituted solution containing an anti-SOST antibody further comprises disaccharide, wherein the disaccharide is trehalose or sucrose.

In an alternative embodiment of the reconstituted solution containing an anti-SOST antibody, the concentration of the disaccharide is 45 mg/mL to 90 mg/ml, preferably 75 mg/ml to 80 mg/ml, most preferably 80 mg/ml.

In an alternative embodiment, the reconstituted solution containing an anti-SOST antibody further comprises a surfactant, wherein the surfactant is polysorbate, preferably polysorbate 80.

In an alternative embodiment of the reconstituted solution containing an anti-SOST antibody, the concentration of the surfactant is 0.3 mg/mL to 0.6 mg/mL, preferably 0.4 mg/ml.

In an alternative embodiment, the reconstituted solution containing an anti-SOST antibody further comprises a viscosity modifier, wherein the viscosity modifier is selected from the group consisting of calcium salt, sodium chloride, magnesium chloride and arginine hydrochloride, preferably the calcium salt is selected from calcium chloride and calcium acetate.

In an alternative embodiment of the reconstituted solution containing an anti-SOST antibody, the concentration of the calcium salt is 4.5 mM to 20 mM, preferably 4.5 mM to 10 mM, most preferably 4.5 mM.

The present disclosure further relates a lyophilized formulation containing an anti-SOST antibody, wherein the lyophilized formulation is reconstituted to form the pharmaceutical composition as described above.

The present disclosure further provides an article or kit, comprising a container containing any of the stable pharmaceutical compositions described herein. In some embodiments, the vial is an injection vial made of neutral borosilicate glass.

The present disclosure further provides use of the pharmaceutical composition, or the lyophilized formulation, or the reconstituted solution as described above, in manufacturing a medicament for the treatment of SOST-related diseases or conditions, wherein the SOST-related diseases or conditions are selected from the group consisting of osteoporosis, osteopenia or osteoarthritis, rheumatoid arthritis, periodontal disease and multiple myeloma, preferably osteoporosis.

The present disclosure further provides a method for treating and preventing a SOST-related disease or condition, comprising administering a therapeutically effective amount of the pharmaceutical composition, or the lyophilized formulation, or the reconstituted solution as described above to a patient in need thereof, wherein the SOST-related disease or condition is selected from the group consisting of osteoporosis, osteopenia or osteoarthritis, rheumatoid arthritis, periodontal disease and multiple myeloma, preferably osteoporosis.

The present disclosure further provides an article comprising a container containing the pharmaceutical composition, or the lyophilized formulation, or the reconstituted solution as described above.

It is appreciated that one, some, or all of the features of the various embodiments described herein can be further combined to obtain other embodiments of the present disclosure. These and other aspects of the disclosure are obvious for those skilled in the art. These and other embodiments of the present disclosure are further described by the following detailed description.

DETAILED DESCRIPTION OF THE DISCLOSURE

Terms

In order to make the disclosure more readily understood, certain technical and scientific terms are specifically defined below. Unless specifically defined otherwise in this document, all other technical and scientific terms used herein shall be taken to have the same meaning as commonly understood by one of ordinary skill in the art to which this disclosure belongs.

"Buffer" refers to a buffer that is resistant to changes in pH because of its conjugate acid-base component. Examples of buffers that control the pH range include acetate buffer, succinate buffer, gluconate buffer, histidine buffer, oxalate buffer, lactate buffer, phosphate buffer, citrate buffer, tartrate buffer, fumarate buffer, glycylglycine and other organic acid buffers.

"Histidine buffer" refers to a buffer comprising histidine ions. Examples of histidine buffers include histidine-hydrochloride buffer, histidine-acetate buffer, histidine-phosphate buffer, histidine-sulfate buffer, etc., preferably histidine-hydrochloride buffer. Histidine-hydrochloride buffer is prepared by combining histidine and hydrochloric acid or histidine and histidine hydrochloride.

"Citrate buffer" refers to a buffer that includes citrate ions. Examples of citrate buffers include citric acid-sodium citrate buffer, citric acid-potassium citrate buffer, citric acid-calcium citrate buffer, citric acid-magnesium citrate buffer, etc. A preferred citrate buffer is citric acid-sodium citrate.

"Succinate buffer" refers to a buffer that includes succinate ions. Examples of succinate buffers include succinic acid-sodium succinate buffer, succinic acid-potassium succinate buffer, succinic acid-calcium succinate buffer, etc. A preferred succinate buffer is succinic acid-sodium succinate buffer.

"Phosphate buffer" refers to a buffer that includes phosphate ions. Examples of phosphate buffers include disodium hydrogen phosphate-sodium dihydrogen phosphate buffer, and disodium hydrogen phosphate-potassium dihydrogen phosphate buffer, etc. A preferred phosphate buffer is disodium hydrogen phosphate-sodium dihydrogen phosphate buffer.

"Acetate buffer" refers to a buffer that includes acetate ions. Examples of acetate buffers include acetic acid-sodium acetate buffer, acetic acid-histidine buffer, acetic acid-potassium acetate buffer, acetic acid-calcium acetate buffer, acetic acid-magnesium acetate buffer, etc. A preferred acetate buffer is acetic acid-sodium acetate buffer.

"Viscosity modifier" is a conventional pharmaceutical material added to adjust the viscosity of the formulation. The viscosity modifier referred to herein generally refers to an inorganic salt and an amino acid salt. Preferably, the inorganic salt is selected from the group consisting of sodium chloride, calcium chloride, magnesium chloride and calcium acetate. Preferably, the amino acid salt is selected from the group consisting of arginine hydrochloride, histidine hydrochloride, glycine hydrochloride, and histidine acetate and the like.

"Pharmaceutical composition" refers to a mixture comprising one or more of the compounds described herein or the physiologically/pharmaceutically acceptable salt thereof or the prodrug thereof with other chemical components. Said other chemical components are, for example, physiological/pharmaceutically acceptable carriers and excipients. The purpose of the pharmaceutical composition is to promote the administration to the organism, which facilitates the absorption of the active ingredient, thereby exerting biological activity. As used herein, "pharmaceutical composition" and "formulation" are not mutually exclusive.

With respect to the solution form of the pharmaceutical composition in the present disclosure, unless otherwise specified, the solvent included therein is water.

"Lyophilized formulation" refers to a formulation or pharmaceutical composition obtained by vacuum freeze-drying a liquid or solution form of pharmaceutical composition or formulation.

The freeze-drying of the present disclosure includes pre-freezing, first drying, and secondary drying. The purpose of pre-freezing is to freeze the product to obtain a crystalline solid. The temperature and speed for the pre-freezing are two important process parameters. In the present disclosure, the temperature for pre-freezing is set to −45° C., and the speed for pre-freezing is set to 1° C./min. The first drying is also known as primary drying, and it is the main stage of freeze-drying. The purpose is to remove the ice from the product while maintaining the shape of the product, minimizing damage to the product. If the temperature and vacuum degree for the primary freezing are not appropriate, it will cause the product to collapse. A higher temperature and greater vacuum degree accelerate the efficiency of lyophilization, but also increase the risk of product collapse. The temperature for primary drying of the present disclosure may be a conventional temperature in the art, for example, −30° C. to 0° C. Secondary drying is also known as analytical drying, and it is the primary step to remove bound water from the product by ultimate vacuum (0.01 mbar) and increasing the temperature (20-40° C.). Since most biological products are sensitive to temperature, the temperature for the secondary drying is chosen to be at the low point of the temperature range, i.e. 25° C. The duration for freeze-drying depends on the freezer, the dose of the lyophilized formulation, and the container comprising the lyophilized agent. Those skilled in the art know how to adjust the duration for freeze-drying.

As used herein, the term "about" refers to a value that is within an acceptable error range for a particular value as determined by one of ordinary skill in the art, which will depend in part on how the value is measured or determined, i.e., the limitations of the measurement system. For example, "about" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values are mentioned in the application and claims, unless otherwise stated, the meaning of "about" or "comprising essentially of" should be assumed to be within an acceptable error range for that particular value.

The pharmaceutical composition of the present disclosure can achieve a stable effect in which the antibody therein substantially retains its physical stability and/or chemical stability and/or biological activity after storage; preferably, the pharmaceutical composition substantially retains the antibody's physical stability, chemical stability and biological activity after storage. The shelf life is generally selected based on the predetermined shelf life of the pharmaceutical composition. There are currently a number of analytical techniques for measuring protein stability that measure stability after storage for a selected period of time at a selected temperature.

A stable antibody pharmaceutical preparation is one in which no significant change is observed in the following conditions: storage at a refrigerated temperature (2-8° C.) for at least 3 months, preferably 6 months, more preferably 1 year, and even more preferably up to 2 years. In addition, a stable liquid preparation includes a liquid preparation that exhibits a desired characteristic upon storage, for example, at a temperature of 25° C. for a period of, for example, 1 month, 3 months, and 6 months, or at 40° C. for 1 month. Generally acceptable criteria for the stability are as follows: typically, no more than about 10%, preferably no more than about 5%, of antibody monomer is degraded, as assessed by SEC-HPLC; the pharmaceutical antibody preparation is colorless or clear to slightly opalescent white by visual analysis; the concentration, pH and osmolality of the preparation have no more than ±10% change; typically, no more than about 10%, preferably no more than about 5% of truncate is observed; typically, no more than about 10%, preferably no more than about 5% of aggregation is formed.

An antibody "retains its physical stability" in a pharmaceutical preparation if it shows no significant increase of aggregation, precipitation and/or denaturation upon visual examination of color and/or clarity, or as measured by UV light scattering, size exclusion chromatography (SEC) or dynamic light scattering (DLS). The changes of protein conformation can be evaluated by fluorescence spectroscopy (which determines the protein tertiary structure), and by FTIR spectroscopy (which determines the protein secondary structure).

An antibody "retains its chemical stability" in a pharmaceutical preparation if it shows no significant chemical alteration. Chemical stability can be assessed by detecting and quantifying chemically altered forms of the protein. Degradation processes that often alter the chemical structure of a protein include hydrolysis or truncating (evaluated by methods such as size exclusion chromatography and SDS-PAGE), oxidation (evaluated by methods such as peptide mapping in conjunction with mass spectroscopy or MALDI/TOF/MS), deamidation (evaluated by methods such as ion-exchange chromatography, capillary isoelectric focusing, peptide mapping, isoaspartic acid measurement), and isomerization (evaluated by measuring the isoaspartic acid content, peptide mapping, etc.).

An antibody "retains its biological activity" in a pharmaceutical preparation if the biological activity of the antibody at a given time is within a predetermined range of the biological activity exhibited at the time the pharmaceutical preparation was prepared. The biological activity of an antibody can be determined, for example, by an antigen binding assay.

As used herein, the term "sclerostin" or "SOST" or "SOST protein" refers to the sclerostin (SOST) gene expression product (protein). Unless otherwise specified, such as the murine SOST (m-SOST) or the cynomolgus monkey SOST (cyno-SOST), this term refers to the human SOST (h-SOST) in the present disclosure. The nucleotide sequences of human, murine and cynomolgus monkey SOST used in the present disclosure are obtained from GenBank, for example, NP_079513.1 provides a human SOST protein sequence.

The three letter codes and single-letter codes for the amino acid residues used herein are described in J. Biol. Chem. 243, p. 3558 (1968).

"Antibody" as used in the present disclosure refers to an immunoglobulin, which is a tetra-peptide chain structure connected by inter-chain disulfide bonds between two identical heavy chains and two identical light chains.

In the present disclosure, the antibody light chain of the present disclosure can further comprise a light chain constant region comprising a human or murine κ or λ, chain, or a variant thereof.

In the present disclosure, the antibody heavy chain of the present disclosure can further comprise a heavy chain constant region comprising a human or murine IgG1, IgG2, IgG3, IgG4, or a variant thereof.

About 110 amino acid residues adjacent to the N-terminus of the antibody heavy and light chains are highly variable, known as the variable regions (Fv regions); the remaining amino acid residues close to the C-terminus are relatively stable, known as the constant regions. The variable regions include three hypervariable regions (HVRs) and four relatively conserved framework regions (FRs). The three hypervariable regions, which determine the specificity of the antibody, are also known as the complementarity determining regions (CDRs). Each light chain variable region (LCVR) and each heavy chain variable region (HCVR) consists of three CDR regions and four FR regions, with a sequential order from the amino terminus to carboxyl terminus as follows: FR1, CDR1, FR2, CDR2, FR3, CDR3, and FR4. The three CDR regions of the light chain are referred to as LCDR1, LCDR2, and LCDR3, and the three CDR regions of the heavy chain are referred to as HCDR1, HCDR2, and HCDR3. The number and position of the CDR amino acid residues in the LCVR and HCVR regions of the antibody or antigen binding fragments herein comply with known Kabat numbering criteria (LCDR1-3, HCDR2-3), or comply with the kabat and chothia numbering criteria (HCDR1).

The antibody of the present disclosure includes a murine antibody, a chimeric antibody or a humanized antibody, preferably a humanized antibody.

The term "murine antibody" in the present disclosure refers to a monoclonal antibody against human SOST prepared according to the knowledge and skills of the field. During the preparation, a test subject is injected with SOST antigen, and then a hybridoma expressing an antibody having the desired sequence or functional properties is separated.

The term "chimeric antibody" is an antibody that is formed by fusing the variable region of a murine antibody with the constant region of a human antibody. A chimeric antibody can alleviate the immune response that is induced by a murine antibody. To construct a chimeric antibody, a hybridoma that secretes a specific murine monoclonal antibody is constructed, and variable region genes are then cloned from the mouse hybridoma cells. Subsequently, constant region genes of a human antibody are cloned as desired. The murine variable region gene is ligated with the human constant region gene to form a chimeric gene that can be inserted into a human vector, and finally a chimeric antibody molecule is expressed in a eukaryotic or prokaryotic industrial system. In a preferred embodiment of the present disclosure, the light chain of the SOST chimeric antibody further comprises the light chain constant regions of a human κ or λ, chain, or a variant thereof, and the heavy chain of the SOST chimeric antibody further comprises the heavy chain constant regions of a human IgG1, IgG2, IgG3, or IgG4, or a variant thereof.

The term "humanized antibody", also referred to as "CDR-grafted antibody", refers to an antibody generated by grafting murine CDR sequences into a variable region framework of a human antibody, namely, an antibody produced from different types of human germline antibody framework sequences. A humanized antibody overcomes the disadvantage of the strong antibody response induced by a chimeric antibody, which carries a large amount of murine protein components. The framework sequences can be obtained from a public DNA database containing germline antibody gene sequences or published references. For example, germline DNA sequences of human heavy and light chain variable region genes can be found in the "VBase" human germline sequence database (available on web www.mrccpe.com.ac.uk/vbase), and can be found in Kabat, E A, et al, 1991 Sequences of Proteins of Immunological Interest, 5th Ed. To avoid a decrease in activity with the decrease in immunogenicity, the framework sequences in the variable region of a human antibody are subjected to minimal reverse mutations or back mutations to maintain the activity. The humanized antibody of the present disclosure also includes a humanized antibody on which CDR affinity maturation is performed by phage display.

The terms "anti-sclerostin antibody", "antibody specifically binding to human sclerostin", "anti-SOST antibody", "anti-SOST", "SOST antibody" and "antibody binding to SOST" in the present disclosure refer to an antibody that is capable of binding to SOST with sufficient affinity, so that the antibody can be used as a diagnostic agent and/or a therapeutic agent for targeting SOST.

The term "binding to SOST" in the present disclosure refers to being capable of interacting with human SOST.

As used herein, the term "specifically binding to" is determined by techniques available in the art, such as competitive ELISA, BIACORE® assay, or KINEXA® assay. The term is also applicable for the case in which the antigen binding domain of the antibody of the disclosure is specific for a particular epitope carried by many antigens. In such case, the antibody carrying the antigen binding domain can specifically bind to a variety of antigens carrying such an epitope.

"Antigen-binding fragment" as used in the present disclosure refers to a Fab fragment, a Fab' fragment, or a F(ab')2 fragment having antigen-binding activity, as well as an scFv fragment binding to human SOST, and other fragments capable of binding to human SOST utilizing the anti-SOST antibody VH and VL. "Antigen-binding fragment" comprises one or more CDR regions of antibodies described in the present disclosure, selected from the group consisting of SEQ ID NO: 3 to SEQ ID NO: 9. An Fv fragment comprises a heavy chain variable region and a light chain variable region, without a constant region, and it is a minimal antibody fragment possessing all antigen-binding sites. Generally, an Fv antibody further comprises a polypeptide linker between the VH and VL domains, and it is capable of forming a structure necessary for antigen binding. Different linkers can be used to connect the variable regions of two antibodies to form a polypeptide chain, referred to as single chain antibody or single chain Fv (scFv).

The term "epitope" refers to a portion of the antigen that can be recognized and bound by one or more antibodies.

"Conservative modifications" or "conservative replacement or substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those skilled in the art recognize that, in general, a single amino acid substitution in non-essential regions of a polypeptide does not substantially alter biological activity (see, e.g., Watson et al. (1987) Molecular Biology of the Gene, The Benjamin/Cummings Pub. Co., p. 224 ($4^{th}$ Ed.)). In addition, substitutions for structurally or functionally similar amino acids are less likely to disrupt biological activity.

"Amino acid identity" refers to sequence similarity between two proteins or between two polypeptides. When a position in both of the two sequences to be compared is occupied by the same amino acid residue, e.g., if a position in each of two polypeptides is occupied by an identical amino acid residue, the molecules are identical at that position. Examples of algorithms suitable for determining percent sequence identity and percent sequence similarity are the BLAST and BLAST 2.0 algorithms, which are described in Altschul et al. (1990) J. Mol. Biol. 215: 403-410 and Altschul et al. (1977) Nucleic Acids Res. 25:3389-3402, respectively. Software for performing BLAST analyses is publicly available at the National Center of Biotechnology Information (www.ncbi.nlm.nih.gov/).

Methods for producing and purifying antibodies and antigen-binding fragments are well known in the art and can be found, for example, in Antibody Experimental Technology Guide of Cold Spring Harbor, Chapters 5-8 and 15. The antibodies or the antigen-binding fragments of the present disclosure are genetically engineered to introduce one or more human framework regions (FRs) to a non-human derived CDR region. Human FR germline sequences can be obtained by comparing the IMGT human antibody variable region germline gene database and MOE software, from ImMunoGeneTics (IMGT) via their website http://imgt.cines.fr, or from *The Immunoglobulin FactsBook*, 2001ISBN012441351.

The engineered antibodies or antigen-binding fragments of the present disclosure can be prepared and purified by conventional methods. For example, cDNA sequences encoding a heavy chain and a light chain can be cloned and recombined into a GS expression vector. The recombined immunoglobulin expression vector can then be stably transfected into CHO cells. As a more recommended method well known in the art, mammalian expression systems result in glycosylation of antibodies, typically at the highly conserved N-terminus in the Fc region. Stable clones can be obtained through expression of an antibody specifically binding to human SOST. Positive clones can be expanded in serum-free culture medium for antibody production in bioreactors. Culture medium, into which an antibody has been secreted, can be purified by conventional techniques. For example, the medium can be conveniently purified by a Protein A or G Sepharose FF column that has been equilibrated with adjusted buffer. The column is washed to remove nonspecific binding components. The bound antibody is eluted by pH gradient, and antibody fragments are detected by SDS-PAGE and then pooled. The antibody can be filtered and concentrated using common techniques. Soluble mixtures and multimers can also be effectively removed by common techniques, including molecular sieve or ion exchange. The obtained product can be immediately frozen, for example at −70° C., or can be lyophilized.

"Administration" and "treatment," when applying to an animal, human, experimental subject, cell, tissue, organ, or biological fluid, refers to contacting an exogenous pharmaceutical, therapeutic, diagnostic agent, or composition with the animal, human, subject, cell, tissue, organ, or biological fluid. "Administration" and "treatment" can refer to, e.g., therapeutic, pharmacokinetic, diagnostic, research, and experimental methods. Treatment of a cell encompasses contacting a reagent with the cell, as well as contacting a reagent with a fluid, where the fluid is in contact with the cell. "Administration" and "treatment" also mean in vitro and ex vivo treatments, e.g., of a cell, by a reagent, diagnostic, binding compound, or by another cell. "Treatment", as it applies to a human, veterinary, or a research subject, refers to therapeutic treatment, prophylactic or preventative measures, or research and diagnostic applications.

"Treat" means to administer a therapeutic agent, such as a composition comprising any of the binding compounds of the present disclosure, internally or externally, to a patient having one or more disease symptoms for which the agent has known therapeutic activity. Typically, the agent is administered in an amount effective to alleviate one or more disease symptoms in the treated patient or population, so as to induce the regression of, or inhibit the progression of, such symptom(s) to any clinically measurable degree. The amount of a therapeutic agent that is effective to alleviate any particular disease symptom (also referred to as a "therapeutically effective amount") may vary according to factors such as the disease state, age, and weight of the patient, and the ability of the drug to elicit a desired response in the patient. Whether a disease symptom has been alleviated can be assessed by any clinical measurement typically used by physicians or other skilled healthcare providers to assess the severity or progression status of that symptom. While an embodiment of the present disclosure (e.g., a treatment method or article of manufacture) may not be effective in alleviating the disease symptom(s) of interest in every patient, it should alleviate the target disease symptom(s) of interest in a statistically significant number of patients as determined by any statistical test known in the art such as the Student's t-test, the chi-square test, the U-test according to Mann and Whitney, the Kruskal-Wallis test (H-test), Jonckheere-Terpstra-test and the Wilcoxon-test.

"Effective amount" encompasses an amount sufficient to ameliorate or prevent a symptom or sign of a medical condition. Effective amount also means an amount sufficient to allow or facilitate diagnosis. An effective amount for a particular patient or veterinary subject can vary depending on factors such as the condition being treated, the general health of the patient, the route and dose of administration, and the severity of side effects. An effective amount can be the maximal dose or dosing protocol that avoids significant side effects or toxic effects.

"Tm value" refers to the thermal denaturation midpoint of the protein, namely, the temperature at which half of the protein is unfolded and the spatial structure of the protein is destroyed. Therefore, the higher the Tm value is, the higher the thermal stability of the protein is.

Embodiments and Test Examples

Hereinafter, the present disclosure is further described with reference to examples. However, the scope of the present disclosure is not limited thereto.

In the examples or test examples of the present disclosure, where specific conditions are not described, the experiments are generally conducted under conventional conditions or in accordance with the conditions suggested by the manufacturer of the raw material or the product. Where the source of the reagents is not specifically given, the reagents are commercially available conventional reagents.

Embodiments

The methods for preparation and purification of the SOST antigen and the antibodies of the present application are disclosed in WO2016145961, with the application date of Feb. 16, 2016, and the application number PCT/CN2016/073857, the entire contents of which are incorporated herein by reference.

Embodiment 1. Production of Monoclonal Anti-Human SOST Antibody

Anti-human SOST monoclonal antibody was produced by immunizing mice. Experimental SJL white 6-week old female mice (Beijing Weitong Lihua Experimental Animal Technology Co., Ltd., animal production license number: SCXK (Beijing) 2012-0001) were used. Feeding environment: SPF level. After the mice were purchased, the animals were kept in the laboratory environment for 1 week, with a 12/12-hour light/dark cycle, at a temperature of 20-25° C., and humidity of 40-60%. The mice that were acclimated to the environment were divided into two groups (A/B), with 10 mice in each group.

Recombinant SOST protein with a His tag (His-h-tag) was used as an immunogen. In group A, Freund's adjuvant (Sigma Lot Num: F5881/F5506) was used for emulsification. The first immunization was performed with Freund's complete adjuvant (CFA), and the booster immunizations were performed with Freund's incomplete adjuvant (IFA). The ratio of antigen to adjuvant was 1:1, 200 μl/200 μg/mouse (first immunization), and 200 μl/100 μg/mouse (booster). In group B, cross-immunization was performed with Titermax (Sigma Lot Num: T2684) and Alum (Thermo Lot Num: 77161). The ratio of antigen to adjuvant (titermax) was 1:1, and the ratio of antigen to adjuvant (Alum) was 3:1, 200 μl/200 μg/mouse (first immunization), and 200 μl/100 μg/mouse (booster). The antigen was emulsified and inoculated on days 0, 14, 28, 42 and 56.

On day 0, the mice in A/B group were intraperitoneally (IP) injected with 50 μg/mouse of the emulsified antigen. On day 14, the mice were subcutaneously (s.c.) injected with 25 μg/mouse at multiple sites (usually 6-8 sites on the back). On days 28 and 42, either back or intraperitoneal injection of the antigen was selected according to the lumps on the back and the swelling conditions in the abdomen. A booster immunization was performed by intraperitoneal (IP) injection of antigen solution formulated with saline at 200 μg/mouse 3 days prior to splenocyte fusion.

Blood tests were performed on days 22, 36, 50, and 64, and the binding activity of mouse serum to human sclerostin was measured by ELISA as described in Test Example 1. The results are shown in Table 1. After the fourth immunization, mice with a high blood titer that was trending to reach a plateau were selected for splenocyte fusion.

Hybridoma cells were obtained by fusing splenocytes with myeloma Sp2/0 cells (ATCC® CRL-8287TM) by using an optimized PEG-mediated fusion procedure. The activity of anti-human SOST antibody in mouse serum to block the binding of human SOST with human LRP-6 was detected according to Test Example 2, and a monoclonal hybridoma cell strain with good in vitro activity, Ab-1, was selected. The results are shown in Table 1.

TABLE 1

The in vitro activity of murine antibody

| candidate antibody | Test example 1-EC50 (nM) | Test example 2-IC50 (nM) |
| --- | --- | --- |
| Ab-1 | 0.701 | 9.91 |

Embodiment 2. Humanization of Murine Anti-Human Sclerostin Antibody

A monoclonal hybridoma cell strain with good in vitro activity, Ab-1, was selected. The sequences of the monoclonal antibody were cloned, and humanization, recombinant expression and activity evaluation were performed.

The process of hybridoma sequencing was performed as follows. The hybridoma cells were collected at logarithmic growth phase, RNA was extracted with Trizol (Invitrogen 15596-018, according to the kit's instructions), and reverse transcription (PrimeScript™ Reverse Transcriptase, Takara, cat #2680A) of the RNA was performed as instructed. The cDNAs obtained by reverse transcription were amplified by PCR using the mouse Ig-Primer Set (Novagen, TB326 Rev.B 0503) and sequenced by a sequencing company. The amino acid sequences corresponding to the obtained DNA sequences are shown as SEQ ID NO: 1 and SEQ ID NO: 2:

```
The heavy chain variable region obtained from
Hybridoma cells:
                                    (SEQ ID NO: 1)
EVQLQQSGPELVKPGTSVKIPCQTSGYTFTDYNLDWLKQRPGESLEWIGD
IDPNNGDILYNQKFRDKATLTVDTSSNTAYLELRSLTSEDTAVYYCARRW
AYYFDYWGQGTTLTISS The light chain variable region obtained from
Hybridoma cells:
                                    (SEQ ID NO: 2)
NIVMTQTPKLLFVSAGDRITITCKASQSVSNDVAWYQQKPGQSPKLLIYY
TSNRFTGVPDRFTGSGYGTDFTLTINTVQAEDLAVYFCQQDYSPVTFGAG
TKLELK
```

The humanization of murine anti-human SOST monoclonal antibody was performed as disclosed in many publications in the art. Briefly, the constant region domain of the parental antibody (murine antibody) was replaced with a human constant region domain, and the human antibody germline was selected according to the homology between the murine and human antibodies. The candidate molecules showing good activity in the present disclosure were humanized and the results are as follows.

1. The CDR regions of murine anti-sclerostin antibody

The amino acid residues of VH/VL CDR were identified and annotated by the Kabat numbering system.

The CDR sequences of murine Ab-1 of the present disclosure are described in Table 2:

TABLE 2

CDR region sequences of murine anti-SOST antibody

| Antibody | Ab-1 |
| --- | --- |
| Heavy chain CDR1 | DYNLD (SEQ ID NO: 3) |
| Heavy chain CDR2 | DIDPNNGDILYNQKFRD (SEQ ID NO: 4) |
| Heavy chain CDR3 | RWAYYFDY (SEQ ID NO: 5) |
| Light chain CDR1 | KASQSVSNDVA (SEQ ID NO: 6) |
| Light chain CDR2 | YTSNRFT (SEQ ID NO: 7) |
| Light chain CDR3 | QQDYSSPVT (SEQ ID NO: 8) |

2. Selecting the human germline FR region sequence

On the basis of the typical VH/VL CDR structure of the obtained murine antibody, the heavy and light chain variable region sequences were compared with the Germline antibody database, and a human germline template with high homology was selected, wherein the framework region of the human germline light chain was from a human kappa light chain gene, and preferably, IGKV1-39*01 or IGKV4-1*01 of the human germline light chain template. The framework region of the human germline heavy chain was from a human heavy chain, and preferably, IGHV1-18*01 of the human germline heavy chain template. The CDR regions of the murine antibody Ab-1 were grafted onto the selected humanized template, replacing the humanized variable region, and then recombined with the IgG constant region. Based on the three-dimensional structure of the murine antibody, back-mutations were performed on the buried residues, on the residues that have direct interactions with the CDR regions, as well as the residues that have important effects on the conformation of VL and VH, and the residues in the CDR regions which exhibit chemical instability were optimized (the heavy chain CDR2 was optimized to obtain a new heavy chain CDR2 sequence, DIDPNDGDI-LYNQKFRD, SEQ ID NO: 9), and a humanized molecule was obtained. The heavy chain variable region sequences of the humanized molecules are shown in SEQ ID NOs: 10-12, and optionally these sequences can be combined with any one of the heavy chain constant regions shown in SEQ ID NOs: 16-18. The light chain variable region sequences of the humanized molecules are shown in SEQ ID NOs: 13-15, and these sequences can be combined with the light chain constant region sequence shown in SEQ ID NO: 19.

1). Heavy chain variable region:

```
Heavy chain variable region of Ab-5:
                                    (SEQ ID NO: 10)
EVQLVQSGAEVKKPGASVKVSCKASGYTFTDYNLDWLRQAPGEGLEWIGD
IDPNDGDILYNQKFRDRVTMTTDTSTSTAYMELRSLRSDDTAVYYCARRW
AYYFDYWGQGTTVTVSS Heavy chain variable region of Ab-9:
                                    (SEQ ID NO: 11)
EVQLVQSGAEVKKPGASVKVSCKASGYTFTDYNLDWLRQAPGEGLEWIGD
IDPNNGDILYNQKFRDRVTMTTDTSTSTAYMELRSLRSDDTAVYYCARRW
AYYFDYWGQGTTVTVSS
```

Heavy chain variable region of Ab-10:
(SEQ ID NO: 12)
EVQLVQSGAEVKKPGASVKVSCKASGYTFTDYNLDWVRQAPGQGLEWMGD
IDPNNGDILYNQKFRDRVTMTTDTSTSTAYMELRSLRSDDTAVYYCARRW
AYYFDYWGQGTTVTVSS 2) The heavy chain constant region of each antibody is optionally selected from the following sequences:

The heavy chain constant region of human IgG4 (K was absent):
(SEQ ID NO: 16)
ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPPCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLSLSLG The heavy chain constant region of human IgG4:
(SEQ ID NO: 17)
ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPPCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLSLSLGK The heavy chain constant region of human IgG2:
(SEQ ID NO: 18)
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK 3) Light chain variable region:

Light chain variable region of Ab-5:
(SEQ ID NO: 13)
DIVMTQSPSSLSASVGDRVTITCKASQSVSNDVAWYQQKPGKSPKLLIYY
TSNRFTGVPDRFSGSGSGTDFTLTISSLQPEDFATYFCQQDYSSPVTFGG
GTKVEIK Light chain variable region of Ab-9:
(SEQ ID NO: 14)
NIVMTQSPSSLSASVGDRVTITCKASQSVSNDVAWYQQKPGKSPKLLIYY
TSNRFTGVPDRFSGSGSGTDFTLTISSLQPEDFATYFCQQDYSSPVTFGG
GTKVEIK Light chain variable region of Ab-10:
(SEQ ID NO: 15)
DIQMTQSPSSLSASVGDRVTITCKASQSVSNDVAWYQQKPGKAPKLLIYY
TSNRFTGVPSRFSGSGSGTDFTLTISSLQPEDFATYYCQQDYSSPVTFGG
GTKVEIK 4) The light chain constant region from human κ chain:
(SEQ ID NO: 19)
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC The antibodies were cloned, expressed and purified by gene cloning and recombinant expression, and then detected by an ELISA binding assay, a blocking assay of antigen-receptor binding, Biacore, cell activity detection, etc. Finally, the humanized antibodies with the best activity, Ab-5, Ab-9, and Ab-10 were selected, and the sequences are shown as follows:

Humanized antibody Ab-10:
Heavy chain:
(SEQ ID NO: 20)
EVQLVQSGAEVKKPGASVKVSCKASGYTFTDYNLDWVRQAPGQGLEWMGD
IDPNNGDILYNQKFRDRVTMTTDTSTSTAYMELRSLRSDDTAVYYCARRW
AYYFDYWGQGTTVTVSSASTKGPSVFPLAPSSKSTSGGTAALGCLVKDYF
PEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK Light chain:
(SEQ ID NO: 23)
DIQMTQSPSSLSASVGDRVTITCKASQSVSNDVAWYQQKPGKAPKLLIYY
TSNRFTGVPSRFSGSGSGTDFTLTISSLQPEDFATYYCQQDYSSPVTFGG
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC Humanized antibody Ab-9:
Heavy chain:
(SEQ ID NO: 21)
EVQLVQSGAEVKKPGASVKVSCKASGYTFTDYNLDWLRQAPGEGLEWIGD
IDPNNGDILYNQKFRDRVTMTTDTSTSTAYMELRSLRSDDTAVYYCARRW
AYYFDYWGQGTTVTVSSASTKGPSVFPLAPCSRSTSESTAALGCLVKDYF
PEPVTVSWNSGALTSGVHTFPAVLQSSGLYSLSSVVTVPSSSLGTKTYTC
NVDHKPSNTKVDKRVESKYGPPCPPCPAPEFLGGPSVFLFPPKPKDTLMI
SRTPEVTCVVVDVSQEDPEVQFNWYVDGVEVHNAKTKPREEQFNSTYRVV
SVLTVLHQDWLNGKEYKCKVSNKGLPSSIEKTISKAKGQPREPQVYTLPP
SQEEMTKNQVSLTCLVKGFYPSDIAVEWESNGQPENNYKTTPPVLDSDGS
FFLYSRLTVDKSRWQEGNVFSCSVMHEALHNHYTQKSLSLSLGK Light chain:
(SEQ ID NO: 24)
NIVMTQSPSSLSASVGDRVTITCKASQSVSNDVAWYQQKPGKSPKLLIYY
TSNRFTGVPDRFSGSGSGTDFTLTISSLQPEDFATYFCQQDYSSPVTFGG
GTKVEIKRTVAAPSVFIFPPSDEQLKSGTASVVCLLNNFYPREAKVQWKV -continued

```
DNALQSGNSQESVTEQDSKDSTYSLSSTLTLSKADYEKHKVYACEVTHQG

LSSPVTKSFNRGEC

Humanized antibody Ab-5:
Heavy chain:
                                         (SEQ ID NO: 22)
EVQLVQSGAEVKKPGASVKVSCKASGYTFTDYNLDWLRQAPGEGLEWIGD

IDPNDGDILYNQKFRDRVTMTTDTSTSTAYMELRSLRSDDTAVYYCARRW

AYYFDYWGQGTTVTVSSASTKGPSVFPLAPCSRSTSESTAALGCLVKDYF

PEPVTVSWNSGALTSGVHTFPAVLQSSGLYSLSSVVTVPSSSLGTKTYTC

NVDHKPSNTKVDKRVESKYGPPCPPCPAPEFLGGPSVFLFPPKPKDTLMI

SRTPEVTCVVVDVSQEDPEVQFNWYVDGVEVHNAKTKPREEQFNSTYRVV

SVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGS

FFLYSRLTVDKSRWQEGNVFSCSVMHEALHNHYTQKSLSLSLG(K)
```

Note: The K at the end of the heavy chain sequence of the humanized antibody Ab-5 may be cleaved during antibody expression, so K may be present or absent at the end of the heavy chain of the final product, but this will not affect the performance of the product itself.

```
Light chain:
                                         (SEQ ID NO: 25)
DIVMTQSPSSLSASVGDRVTITCKASQSVSNDVAWYQQKPGKSPKLLIYY

TSNRFTGVPDRFSGSGSGTDFTLTISSLQPEDFATYFCQQDYSSPVTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

Exemplary Process for Preparation of Antibody Pharmaceutical Compositions (Formulations)

Step 1: A drug substance solution comprising an anti-SOST antibody with an anti-SOST antibody (such as Ab-5) and stable agent(s) is prepared, filtrated, and sampled for a sterility test. The drug substance solution was passed through a 0.22 μm PVDF filter, and the filtrate was collected.

Step 2: The filtrate is adjusted to a loading volume of 1.1 ml and loaded into a 2 ml vial with a stopper. The volume differences are detected by sampling at the beginning, middle and end of the loading procedure.

Step 3: An aluminum cap is capped using a capping machine.

Step 4: Visual inspection is performed to confirm whether there is any defect such as inaccurate loading. A label is printed and pasted onto the vial. The vials are placed into a paper tray, and a label is printed and pasted onto the paper tray.

Embodiment 3. Screening Buffer System

Anti-SOST antibody Ab-5 formulation samples with a protein concentration of 80 mg/ml were prepared using the following buffers:
1) 10 mM acetic acid-sodium acetate, pH 5.0
2) 10 mM histidine-acetic acid, pH 5.0
3) 10 mM histidine-acetic acid, pH 5.5
4) 10 mM disodium hydrogen phosphate-citric acid, pH 5.5
5) 10 mM disodium hydrogen phosphate-citric acid, pH 7.0
6) 10 mM disodium hydrogen phosphate-citric acid, pH 7.5

When the anti-SOST antibody Ab-5 was replaced in pH 7.0 and 7.5 buffers, the protein completely precipitated. Combined with the antibody's isoelectric point range, this indicates that the pH of the buffer should be no more than 5.5.

The successfully replaced formulation sample was filled into a 2 mL vial, at a volume of 1.5 mL/vial, sealed with a chlorinated butyl rubber stopper, and shaken (25° C., 300 rpm) to monitor the stability. After shaking for 3 days, the disodium hydrogen phosphate-citric acid (pH 5.5) system was completely turbid. The histidine-acetic acid system showed a milky white appearance after shaking, and the acetic acid system showed a small amount of precipitate. The SEC purity did not change significantly in the systems. Therefore, the buffer system for the anti-SOST antibody formulation may be a histidine-acetic acid system or an acetic acid-sodium acetate system, and the pH range should be 5.0-5.5. Among the systems, acetic acid-sodium acetate (pH 5.0) was a relatively better buffer system. See Table 3:

TABLE 3

Stability of Ab-5 in different pH and buffer systems after shaking for three days

| Buffer system | Time | SEC(%) | | DLS | | Appearance |
| | | Monomer | Polymer | Z-Ave Mean(d · nm) | PdI | |
| --- | --- | --- | --- | --- | --- | --- |
| 10 mM acetic acid-sodium acetate pH5.0 | 0 | 96.9 | 1.6 | 17.07 | 0.135 | Clear and transparent |
| | 3 days | 97.5 | 1.6 | 27.55 | 0.317 | Transparent, Small amount of precipitation |
| 10 mM histidine-acetic acid pH5.0 | 0 | 96.9 | 1.6 | 20.06 | 0.147 | Clear and transparent |
| | 3 days | 97.2 | 1.9 | 358.2 | 0.807 | White opalescence |

TABLE 3-continued

Stability of Ab-5 in different pH and buffer systems after shaking for three days

| Buffer system | Time | SEC(%) Monomer | SEC(%) Polymer | DLS Z-Ave Mean(d · nm) | PdI | Appearance |
|---|---|---|---|---|---|---|
| 10 mM histidine-acetic acid pH5.5 | 0 | 97.0 | 1.6 | 37.09 | 0.124 | Light Blue opalescence |
|  | 3 days | 97.5 | 1.6 | 556.3 | 1.000 | White opalescence, small amount of precipitation |
| 10 mM disodium hydrogen phosphate-citric acid pH5.5 | 0 | 96.9 | 1.6 | 33.98 | 0.096 | Light Blue opalescence |
|  | 3 days | 93.6 | 6.2 | 36.51 | 0.211 | Turbid |

Anti-SOST antibody formulation samples with a protein concentration of 85 mg/ml were prepared using the following buffers:
1) 10 mM acetic acid-sodium acetate, pH 4.8
2) 10 mM acetic acid-sodium acetate, pH 5.0
3) 10 mM acetic acid-sodium acetate, pH 5.2
4) 30 mM acetic acid-sodium acetate, pH5.0
5) 10 mM succinic acid-sodium succinate, pH5.0

The formulation sample was filled into a 2 mL vial, at a volume of 1.5 mL/vial, sealed with a chlorinated butyl rubber stopper, shaken (25° C., 300 rpm) and illuminated (4500 Lx) to monitor the stability. After shaking for 3 days, the 10 mM acetic acid-sodium acetate (pH 4.8) and the 10 mM succinic acid-sodium succinate (pH 5.0) systems were completely turbid. The stability of the 10 mM acetic acid-sodium acetate (pH 5.0) and 30 mM acetic acid-sodium acetate (pH 5.0) systems were relatively good, and there was no significant difference between the two systems. After 10 days of light exposure, the IEC main peak purity of the anti-SOST antibody of the 10 mM acetic acid-sodium acetate (pH 5.0) and the 10 mM acetic acid-sodium acetate (pH 5.2) systems was decreased less than that of the other three groups. Therefore, the optimal buffer system for the anti-SOST antibody formulation was an acetic acid-sodium acetate system, and the concentration may be 10-30 mM, preferably 10 mM, and the pH should be greater than 4.8.

TABLE 4

Stability of Ab-5 in different pH, ionic strength and buffer systems after shaking for three days

| Buffer system | Time | SEC(%) Monomer | SEC(%) Polymer | DLS Z-Ave Mean (d · nm) | PdI | Appearance |
|---|---|---|---|---|---|---|
| 10 mM Acetic acid-sodium acetate pH4.8 | 0 | 97.2 | 1.5 | 20.31 | 0.517 | Light Blue opalescence |
|  | 3 Days | 95.5 | 3.7 | 266.4 | 0.445 | Turbid |
| 10 mM Acetic acid-sodium acetate pH5.0 | 0 | 97.3 | 1.5 | 18.65 | 0.153 | Clear and transparent |
|  | 3 Days | 97.5 | 1.6 | 249.4 | 0.421 | White opalescence |
| 10 mM Acetic acid-sodium acetate pH5.2 | 0 | 97.3 | 1.5 | 28.63 | 0.130 | Light Blue opalescence |
|  | 3 Days | 97.5 | 1.6 | 928.3 | 1.000 | White opalescence |
| 30 mM Acetic acid-sodium acetate pH5.0 | 0 | 97.0 | 1.5 | 23.05 | 0.119 | Clear and transparent |
|  | 3 Days | 97.5 | 1.6 | 454.6 | 0.667 | White opalescence |
| 10 mM Succinic acid-sodium succinate pH5.0 | 0 | 97.2 | 1.5 | 30.41 | 0.090 | Light blue opalescence |
|  | 3 Days | N/A | N/A | 2022 | 0.496 | Turbid |

TABLE 5

Stability of Ab-5 in different pH, ionic strength and buffer systems after light exposure for ten days

| Buffer system | Time | SEC(%) Monomer | SEC(%) Polymer | IEC(%) Main peak | IEC(%) Acid peak | IEC(%) Alkaline peak | Appearance |
|---|---|---|---|---|---|---|---|
| 10 mM Acetic acid-sodium acetate pH4.8 | 0 | 97.2 | 1.5 | 70.9 | 20.0 | 9.1 | Light blue opalescence |
| | 3 days | 96.5 | 2.5 | 38.3 | 16.1 | 45.6 | Transparent, small amount of precipitation |
| 10 mM Acetic acid-sodium acetate pH5.0 | 0 | 97.3 | 1.5 | 71.1 | 20.0 | 8.9 | Clear and transparent |
| | 3 days | 96.5 | 2.6 | 40.4 | 17.4 | 42.3 | Transparent, small amount of precipitation |
| 10 mM Acetic acid-sodium acetate pH5.2 | 0 | 97.3 | 1.5 | 70.7 | 20.2 | 9.1 | Light blue opalescence |
| | 3 days | 96.1 | 2.7 | 42.5 | 17.1 | 40.4 | Light blue opalescence, small amount of precipitation |
| 30 mM Acetic acid-sodium acetate pH5.0 | 0 | 97.0 | 1.5 | 70.9 | 20.2 | 8.9 | Clear and transparent |
| | 3 days | 96.6 | 2.3 | 38.5 | 15.6 | 45.9 | Transparent, small amount of precipitation |
| 10 mM Succinic acid-sodium succinate pH5.0 | 0 | 97.2 | 1.5 | 71.1 | 20.2 | 8.7 | Light blue opalescence |
| | 3 days | 96.5 | 2.6 | 37.1 | 15.9 | 47.0 | Light blue opalescence, small amount of precipitation |

Embodiment 4. Screening Saccharides in the Formulation

Anti-SOST antibody solutions were prepared in 10 mM succinic acid-sodium succinate buffer, pH5.5, wherein the concentration of Ab-5 protein was 1 mg/ml and the solutions comprised 4.5%, 6%, 7.5% and 9% of α, α-dihydrate trehalose or 6% sucrose. The thermal stability of the anti-SOST antibody in the different formulations was measured by differential scanning calorimetry (DSC). The results showed that the initial denaturation temperature ($Tm_{onset}$) of f anti-SOST antibody Ab-5 was gradually increased with the increase of the concentration of saccharide, and the $Tm_{onset}$ with trehalose was significantly higher than that with sucrose. It indicates that the anti-SOST antibody has better thermal stability in a formulation with a relatively higher concentration of trehalose.

In view of the osmotic pressure required for the injection solution, 8% α,α-dihydrate trehalose was considered to be the most preferred condition.

TABLE 6

Thermal stability of Ab-5 in different types and concentrations of saccharide

| Saccharide types | Concentration of Saccharide (mg/ml) | $Tm_{onset}$ (° C.) | Tm1 (° C.) | Tm2 (° C.) |
|---|---|---|---|---|
| α,α-dihydrate trehalose | 45 | 58.19 | 67.00 | 81.15 |
| | 60 | 58.71 | 67.25 | 81.14 |
| | 75 | 57.72 | 67.61 | 81.49 |
| | 90 | 60.37 | 67.58 | 81.48 |
| sucrose | 60 | 56.92 | 67.08 | 81.24 |

Note: In the present disclosure, a sugar concentration of 6% is equivalent to 60 mg/ml; a concentration of 9% is equivalent to 90 mg/ml, and the other unit conversions follow this rule.

Embodiment 5. Screening Viscosity Modifiers in the Formulation

In order to reduce the viscosity of the formulation, the following viscosity modifiers were added to a solution containing 30 mg/ml anti-SOST antibody, 10 mM acetic acid-sodium acetate, pH5.0, to determine whether the viscosity can be lowered while improving the ultrafiltration efficiency.

1) 90 mg/ml α, α-dihydrate trehalose
2) 70 mg/ml α, α-dihydrate trehalose+40 mM sodium chloride
3) 90 mg/ml α, α-dihydrate trehalose+10 mM calcium chloride
4) 90 mg/ml α, α-dihydrate trehalose+10 mM magnesium chloride
5) 150 mM sodium chloride
6) 140 mM arginine hydrochloride
7) 10 mM calcium acetate
8) 20 mM calcium chloride
9) 4.5 mM calcium chloride The experimental results showed that saccharide did not help to improve the ultrafiltration efficiency. Sodium chloride and arginine hydrochloride could increase the ultrafiltration efficiency moderately, while calcium and magnesium salts greatly improved the ultrafiltration efficiency. The concentration of the calcium salt may range from 4.5 to 20 mM, and there was no significant difference in the ultrafiltration efficiency in this range.

Embodiment 6. Screening Surfactants in the Formulation

Anti-SOST antibody formulation samples containing different protein concentrations were prepared in buffers with different concentrations and types of surfactants, wherein the buffer comprised 10 mM acetic acid-sodium acetate (pH 5.0), 4.5 mM calcium chloride, 80 mg/ml α, α-dihydrate trehalose. Experimental design and analysis was performed by DoE as follows:

1) Protein concentration: 80~100 mg/ml
2) Type of surfactant: Polysorbate 20 (PS20), Polysorbate 80 (PS80)
3) Polysorbate concentration: 0.02~0.8 mg/ml The formulations were added into a 1 ml BD administration syringe at 1.2 ml/branch and were shaken at 25° C./300 rpm/12 days. The results showed that there was no significant change in the purity via SEC, non-reduced CE-SDS and IEC assays after 12 days of shaking. The results showed good compatibility of the SOST antibody formulations with the drug delivery device. At the same time, MFI was used to detect the number of sub-visible particles larger than 2 μm and the changes, showing significant differences between the various formulations. According to the DoE fitting results (an effective fitting model), the increase in the number of particles could be controlled within 500 by using polysorbate 80 and a protein concentration of higher than 96 mg/ml. Further, when the concentration of polysorbate 80 was set at about 0.3-0.6 mg/ml, the number of particles in the formulation was the least at 0 point.

TABLE 7

Shaking stability (purity) of different concentrations of Ab-5 in different types and concentrations of Tween

| Concentration of protein (mg/ml) | Concentration of Tween (mg/ml) | Tween type | Time | % SEC Polymer | Monomer | Fragmentation | % Non-reduced CE-SDS | % IEC Acid peak | Main peak | Alkaline peak |
|---|---|---|---|---|---|---|---|---|---|---|
| 80 | 0.02 | PS20 | 0 | 0.6 | 99.0 | 0.4 | 96.8 | 11.9 | 76.6 | 11.5 |
|  |  |  | 12 days | 0.8 | 98.5 | 0.7 | 96.5 | 12.3 | 76.6 | 11.1 |
| 100 | 0.80 | PS20 | 0 | 0.6 | 98.7 | 0.7 | 96.9 | 11.9 | 76.7 | 11.3 |
|  |  |  | 12 days | 0.8 | 98.2 | 1.0 | 96.1 | 12.3 | 76.6 | 11.1 |
| 80 | 0.80 | PS20 | 0 | 0.6 | 98.8 | 0.6 | 96.5 | 11.9 | 76.7 | 11.4 |
|  |  |  | 12 days | 0.8 | 98.3 | 1.0 | 96.4 | 12.1 | 77.0 | 10.8 |
| 100 | 0.02 | PS20 | 0 | 0.6 | 98.9 | 0.5 | 97.0 | 12.0 | 76.7 | 11.3 |
|  |  |  | 12 days | 0.8 | 98.4 | 0.8 | 96.0 | 12.3 | 76.9 | 10.8 |
| 80 | 0.41 | PS80 | 0 | 0.6 | 98.8 | 0.6 | 96.8 | 11.9 | 76.8 | 11.3 |
|  |  |  | 12 days | 0.8 | 98.5 | 0.8 | 95.9 | 12.6 | 76.1 | 11.4 |
| 90 | 0.41 | PS20 | 0 | 0.6 | 98.5 | 0.8 | 96.9 | 12.0 | 76.7 | 11.4 |
|  |  |  | 12 days | 0.8 | 98.5 | 0.7 | 96.3 | 12.3 | 77.1 | 10.6 |
| 100 | 0.41 | PS80 | 0 | 0.7 | 98.6 | 0.8 | 97.0 | 12.0 | 76.8 | 11.2 |
|  |  |  | 12 days | 0.8 | 98.2 | 1.0 | 96.3 | 12.7 | 76.4 | 10.9 |
| 90 | 0.41 | PS20 | 0 | 0.6 | 98.9 | 0.5 | 96.6 | 12.0 | 76.8 | 11.2 |
|  |  |  | 12 days | 0.8 | 98.2 | 1.0 | 95.9 | 12.2 | 77.2 | 10.6 |
| 90 | 0.02 | PS80 | 0 | 0.6 | 98.7 | 0.7 | 96.7 | 12.0 | 76.9 | 11.2 |
|  |  |  | 12 days | 0.8 | 98.2 | 1.0 | 96.4 | 12.3 | 76.5 | 11.2 |
| 90 | 0.80 | PS80 | 0 | 0.6 | 98.6 | 0.8 | 96.8 | 11.9 | 76.7 | 11.4 |
|  |  |  | 12 days | 0.8 | 98.5 | 0.8 | 96.5 | 12.2 | 77.0 | 10.7 |

TABLE 8

Shaking stability (SVP) of different concentrations of Ab-5 in different types and concentrations of Tween

| Concentration of protein (mg/ml) | Concentration of Tween (mg/ml) | Tween type | Time | Number of Particles larger than 2 μm | Increase in the number of particle |
|---|---|---|---|---|---|
| 80 | 0.02 | PS20 | 0 | 224 | 675 |
|  |  |  | 12 days | 899 |  |
| 100 | 0.80 | PS20 | 0 | 1124 | 553 |
|  |  |  | 12 days | 1677 |  |
| 80 | 0.80 | PS20 | 0 | 325 | 1120 |
|  |  |  | 12 days | 1445 |  |
| 100 | 0.02 | PS20 | 0 | 461 | 1077 |
|  |  |  | 12 days | 1538 |  |
| 80 | 0.41 | PS80 | 0 | 1663 | 2105 |
|  |  |  | 12 days | 3768 |  |
| 90 | 0.41 | PS20 | 0 | 100 | 3514 |
|  |  |  | 12 days | 3614 |  |
| 100 | 0.41 | PS80 | 0 | 1224 | −95 |
|  |  |  | 12 days | 1129 |  |
| 90 | 0.41 | PS20 | 0 | 362 | 2072 |
|  |  |  | 12 days | 2434 |  |
| 90 | 0.02 | PS80 | 0 | 2037 | 1066 |
|  |  |  | 12 days | 3103 |  |
| 90 | 0.80 | PS80 | 0 | 1927 | 1816 |
|  |  |  | 12 days | 3743 |  |

Embodiment 7. Study on Stability of the Ingredients of the Formulation

Ab-5 was prepared at 100 mg/mL in 10 mM acetic acid-sodium acetate buffer (pH 5.0), containing 4.5 mM calcium chloride, 80 mg/mL α, α-dihydrate trehalose or sucrose, 0.4 mg/mL polysorbate 20 or 80. The formulation was filled into a 2 mL vial at 1.5 mL/bottle, sealed with a chlorinated butyl rubber stopper, and placed at 25° C. and 2 to 8° C., to monitor the stability. The results showed that a large amount of small particles appeared in the formulation containing polysorbate 20 after placing at 2-8° C. for 6 months, which was not suitable for an anti-SOST antibody Ab-5 formulation. With respect to the formulation containing polysorbate 80, there was no significant difference between trehalose and sucrose, and the formulation showed good stability at 25° C. for 3 months or at 2 to 8° C. for 6 months.

TABLE 9

Stability of formulations containing different types of saccharide and tween at 25° C.

| Saccharide type | Tween type | Time (month) | % SEC Polymer | Monomer | Fragmentation | % Non-reduced CE-SDS | % IEC Acid peak | Main peak | Alkaline peak | Appearance |
|---|---|---|---|---|---|---|---|---|---|---|
| Sucrose | PS20 | 0 | 0.8 | 98.0 | 1.2 | 93.3 | 19.7 | 72.3 | 8.1 | Clear |
|  |  | 1 | 1.4 | 98.2 | 0.5 | 96.5 | 20.2 | 70.4 | 9.4 | Clear |
|  |  | 2 | 1.6 | 97.5 | 0.9 | 96.4 | 22.3 | 71.9 | 5.8 | Clear, small amount of particles |
|  |  | 3 | 1.8 | 97.1 | 1.1 | 95.6 | 22.6 | 65.5 | 11.9 | Clear, small amount of particles |
| Sucrose | PS80 | 0 | 0.8 | 98.3 | 0.9 | 93.5 | 19.9 | 72.4 | 7.7 | Clear |
|  |  | 1 | 1.4 | 98.2 | 0.4 | 96.2 | 20.2 | 70.5 | 9.4 | Clear |
|  |  | 2 | 1.6 | 97.4 | 1.0 | 96.3 | 22.2 | 72.0 | 5.9 | Clear, small amount of particles |
|  |  | 3 | 1.8 | 97.2 | 1.1 | 95.4 | 22.6 | 65.3 | 12.1 | Clear, small amount of particles |
| Trehalose | PS20 | 0 | 0.8 | 98.3 | 0.9 | 93.4 | 19.8 | 72.1 | 8.1 | Clear |
|  |  | 1 | 1.4 | 98.1 | 0.5 | 96.1 | 20.2 | 70.8 | 9.0 | Clear |
|  |  | 2 | 1.7 | 97.3 | 1.1 | 96.1 | 22.2 | 72.0 | 5.8 | Clear, small amount of particles |
|  |  | 3 | 1.8 | 97.0 | 1.2 | 95.8 | 22.7 | 65.5 | 11.9 | Clear, small amount of particles |
| Trehalose | PS80 | 0 | 0.8 | 98.3 | 0.9 | 93.5 | 19.9 | 72.4 | 7.7 | Clear |
|  |  | 1 | 1.4 | 98.2 | 0.4 | 96.3 | 20.2 | 70.6 | 9.2 | Clear |
|  |  | 2 | 1.7 | 97.4 | 0.9 | 96.3 | 22.3 | 72.0 | 5.7 | Clear, small amount of particles |
|  |  | 3 | 1.8 | 97.1 | 1.1 | 95.8 | 22.7 | 65.3 | 12.0 | Clear, small amount of particles |

TABLE 10

Stability of formulations containing different types of saccharide and tween at 2-8° C.

| Saccharide type | Tween type | Time (month) | % SEC Polymer | Monomer | Fragmentation | % Non-reduced CE-SDS | % IEC Acid peak | Main peak | Alkaline peak | Appearance |
|---|---|---|---|---|---|---|---|---|---|---|
| Sucrose | PS20 | 0 | 0.8 | 98.0 | 1.2 | 93.3 | 19.7 | 72.3 | 8.1 | Clear |
|  |  | 1 | 0.9 | 98.7 | 0.4 | 96.4 | 19.2 | 72.4 | 8.4 | Clear |
|  |  | 3 | 1.0 | 98.1 | 0.9 | 96.5 | 18.8 | 71.3 | 9.8 | Clear |
|  |  | 6 | 1.2 | 98.2 | 0.7 | 97.5 | 19.5 | 70.8 | 9.7 | Large amount of small particles |
| Sucrose | PS80 | 0 | 0.8 | 98.3 | 0.9 | 93.5 | 19.9 | 72.4 | 7.7 | Clear |
|  |  | 1 | 0.9 | 98.7 | 0.4 | 96.8 | 19.4 | 72.7 | 7.9 | Clear |
|  |  | 3 | 1.0 | 98.0 | 1.0 | 96.4 | 18.8 | 71.7 | 9.5 | Clear |
|  |  | 6 | 1.2 | 98.3 | 0.5 | 97.4 | 19.4 | 71.1 | 9.5 | Clear |
| Trehalose | PS20 | 0 | 0.8 | 98.3 | 0.9 | 93.4 | 19.8 | 72.1 | 8.1 | Clear |
|  |  | 1 | 0.9 | 98.7 | 0.4 | 96.4 | 19.3 | 72.7 | 8.0 | Clear |
|  |  | 3 | 1.0 | 98.0 | 1.0 | 96.4 | 18.8 | 71.2 | 10.0 | Clear |
|  |  | 6 | 1.3 | 98.2 | 0.6 | 97.5 | 19.2 | 71.2 | 9.6 | Large amount of small particles |
| Trehalose | PS80 | 0 | 0.8 | 98.3 | 0.9 | 93.5 | 19.9 | 72.4 | 7.7 | Clear |
|  |  | 1 | 0.9 | 98.6 | 0.4 | 96.2 | 19.3 | 72.8 | 7.9 | Clear |
|  |  | 3 | 1.0 | 98.1 | 0.9 | 96.3 | 18.9 | 71.5 | 9.6 | Clear |
|  |  | 6 | 1.2 | 98.2 | 0.6 | 97.4 | 19.4 | 70.9 | 9.7 | Clear |

Embodiment 8. Lyophilization of the Formulation

Anti-SOST antibody formulation samples were prepared in a buffer containing 10 mM acetic acid-sodium acetate pH 5.0, 80 mg/ml trehalose, 0.4 mg/ml polysorbate 80, and 4.5 mM calcium chloride, and the concentration of anti-SOST antibody protein was 100 mg/ml. The formulation was filled into a 2 mL vial at 1.1 mL/vial, placed in a lyophilization box, and lyophilized. The lyophilization procedure included pre-freezing, primary drying and secondary drying. After the lyophilization procedure was finished, a plug was inserted under vacuum. The reconstituted samples were compared to those before and after the lyophilization procedure. The results showed that the reconstituted solutions maintained good performance of the liquid formulation.

TABLE 11

Lyophilization procedure

| Freeze-drying process parameters | Temperature (° C.) | Vacuum degree (mBar) |
|---|---|---|
| pre-freezing | 5 | N/A |
|  | −45 | N/A |
| primary drying | −27 | 0.1 |
| secondary drying | 25 | 0.01 |

Embodiment 9. Alternative Formulations

The stable pharmaceutical formulation provided by the present disclosure may also be a stable combination selected from the following:

(1) 120 mg/ml anti-SOST antibody Ab-5, 95 mg/ml trehalose, 0.5 mg/ml polysorbate 80, 5 mM acetic acid-sodium acetate buffer and 15 mM calcium chloride, final pH of 5.5;

(2) 120 mg/ml anti-SOST antibody Ab-5, 95 mg/ml trehalose, 0.5 mg/ml polysorbate 80, 5 mM acetic acid-sodium acetate buffer and 15 mM calcium chloride, final pH of 5.4;

(3) 120 mg/ml anti-SOST antibody Ab-5, 95 mg/ml trehalose, 0.5 mg/ml polysorbate 80, 5 mM acetic acid-sodium acetate buffer and 15 mM calcium chloride, final pH of 5.3;

(4) 120 mg/ml anti-SOST antibody Ab-5, 95 mg/ml trehalose, 0.5 mg/ml polysorbate 80, 5 mM acetic acid-sodium acetate buffer and 15 mM calcium chloride, final pH is 5.1;

(5) 120 mg/ml anti-SOST antibody Ab-5, 95 mg/ml trehalose, 0.5 mg/ml polysorbate 80, 5 mM acetic acid-sodium acetate buffer and 15 mM calcium chloride, final pH of 4.9;

(6) 120 mg/ml anti-SOST antibody Ab-5, 95 mg/ml trehalose, 0.5 mg/ml polysorbate 80, 5 mM acetic acid-sodium acetate buffer and 15 mM calcium chloride, final pH of 4.8;

(7) 110 mg/ml anti-SOST antibody Ab-5, 40 mg/ml trehalose, 0.5 mg/ml polysorbate 80, 20 mM acetic acid-sodium acetate buffer and 7.5 mM calcium chloride, final pH of 5.4;

(8) 110 mg/ml anti-SOST antibody Ab-5, 40 mg/ml trehalose, 0.5 mg/ml polysorbate 80, 20 mM acetic acid-sodium acetate buffer and 7.5 mM calcium chloride, final pH of 5.3;

(9) 110 mg/ml anti-SOST antibody Ab-5, 40 mg/ml trehalose, 0.5 mg/ml polysorbate 80, 20 mM acetic acid-sodium acetate buffer and 7.5 mM calcium chloride, final pH of 5.1;

(10) 110 mg/ml anti-SOST antibody Ab-5, 40 mg/ml trehalose, 0.5 mg/ml polysorbate 80, 20 mM acetic acid-sodium acetate buffer and 7.5 mM calcium chloride, final pH of 4.9;

(11) 100 mg/ml anti-SOST antibody Ab-5, 50 mg/ml trehalose, 0.5 mg/ml polysorbate 80, 20 mM acetic acid-sodium acetate buffer and 6.0 mM calcium chloride, final pH of 4.9;

(12) 100 mg/ml anti-SOST antibody Ab-5, 50 mg/ml trehalose, 0.5 mg/ml polysorbate 80, 20 mM acetic acid-sodium acetate buffer and 6.0 mM calcium chloride, final pH of 5.1;

(13) 100 mg/ml anti-SOST antibody Ab-5, 50 mg/ml trehalose, 0.5 mg/ml polysorbate 80, 20 mM acetic acid-sodium acetate buffer and 6.0 mM calcium chloride, final pH of 5.3;

(14) 100 mg/ml anti-SOST antibody Ab-5, 50 mg/ml trehalose, 0.5 mg/ml polysorbate 80, 20 mM acetic acid-sodium acetate buffer and 6.0 mM calcium chloride, final pH of 5.4.

(15) 90 mg/ml anti-SOST antibody Ab-5, 40 mg/ml trehalose, 0.3 mg/ml polysorbate 80, 5 mM acetic acid-sodium acetate buffer (pH 4.8) and 15 mM calcium chloride;

(16) 110 mg/ml anti-SOST antibody Ab-5, 95 mg/ml trehalose, 0.6 mg/ml polysorbate 80, 20 mM acetic acid-sodium acetate buffer (pH 5.5) and 20 mM calcium chloride;

(17) 100 mg/ml anti-SOST antibody Ab-5, 80 mg/ml trehalose, 0.4 mg/ml polysorbate 80, 10 mM acetic acid-sodium acetate buffer (pH 5.0) and 4.5 mM calcium chloride.

What is claimed is:

1. A pharmaceutical composition comprising:
an anti-sclerostin antibody or antigen-binding fragment thereof at a concentration of 60 mg/ml to 120 mg/ml;
an acetate buffer at a concentration of 5 mM to 30 mM;
a trehalose at a concentration of 40 mg/ml to 95 mg/ml;
a polysorbate 80 at a concentration of 0.02 mg/ml to 0.8 mg/ml; and
a calcium salt viscosity modifier at a concentration of 4.5 mM to 20 mM;
wherein the pharmaceutical composition has a pH of 4.8 to 5.5;
wherein the anti-sclerostin antibody or antigen-binding fragment thereof comprises a heavy chain variable region comprising HCDR1, HCDR2 and HCDR3 having the amino acid sequences of SEQ ID NO: 3, SEQ ID NO: 9 and SEQ ID NO: 5, respectively, and a light chain variable region comprising LCDR1, LCDR2 and LCDR3 having the amino acid sequences of SEQ ID NO: 6, SEQ ID NO: 7 and SEQ ID NO: 8, respectively.

2. The pharmaceutical composition of claim 1, wherein the anti-sclerostin antibody or antigen-binding fragment thereof comprises a heavy chain variable region having the amino acid sequence of SEQ ID NO: 10, and a light chain variable region having the amino acid sequence of SEQ ID NO: 13.

3. The pharmaceutical composition of claim 2, wherein the light chain amino acid sequence of the anti-sclerostin antibody has the sequence of SEQ ID NO: 25, and the heavy chain amino acid sequence of the anti-sclerostin antibody has the sequence of SEQ ID NO: 22.

4. A pharmaceutical composition, comprising:
an anti-sclerostin antibody or antigen-binding fragment thereof at a concentration of 90 mg/ml to 120 mg/ml, wherein the anti-sclerostin antibody or antigen-binding fragment thereof comprises a heavy chain variable region comprising HCDR1, HCDR2 and HCDR3 having the amino acid sequences of SEQ ID NO: 3, SEQ ID NO: 9 and SEQ ID NO: 5, respectively, and a light chain variable region comprising LCDR1, LCDR2 and LCDR3 having the amino acid sequences of SEQ ID NO: 6, SEQ ID NO: 7 and SEQ ID NO: 8, respectively;
an acetate buffer at a concentration of 10 mM to 20 mM;
a trehalose at a concentration of 45 mg/ml to 90 mg/ml;
a polysorbate 80 at a concentration of 0.3 mg/ml to 0.6 mg/ml; and
a viscosity modifier of calcium salt at a concentration of 4.5 mM to 10 mM;
wherein the acetate buffer has a pH of 5.0 to 5.5.

5. The pharmaceutical composition of claim 4, comprising:
the anti-sclerostin antibody at a concentration of 100 mg/ml; wherein the anti-sclerostin antibody comprises a light chain having the amino acid sequence of SEQ ID NO: 25, and a heavy chain having the amino acid sequence of SEQ ID NO: 22;
an acetate buffer at a concentration of 10 mM;
trehalose at a concentration of 80 mg/ml;
polysorbate 80 at a concentration of 0.4 mg/ml; and
a calcium salt at a concentration of 4.5 mM;
wherein the acetate buffer has a pH of 5.0.

6. A method for preparing a lyophilized formulation, the method comprising freeze-drying the pharmaceutical composition of claim 1, wherein the freeze-drying comprises the sequential steps of pre-freezing, primary drying and secondary drying.

7. A lyophilized formulation prepared by the method of claim 6.

8. A method for preparing a reconstituted solution, comprising reconstituting the lyophilized formulation of claim 7 with a solvent for reconstitution, wherein the solvent for reconstitution is water for injection.

9. A reconstituted solution prepared by the method of claim 8.

10. The reconstituted solution of claim 9, comprising the anti-sclerostin antibody or antigen-binding fragment thereof at a concentration of 80 mg/ml to 100 mg/ml, and further comprising an acetic acid-sodium acetate buffer at a concentration of 10 mM to 30 mM, the trehalose at a concentration of 45 mg/ml to 90 mg/ml, the polysorbate 80 at a concentration of 0.3 mg/ml to 0.6 mg/ml, and the calcium salt viscosity modifier at a concentration of 4.5 mM to 20 mM, wherein the reconstituted solution has a pH of 4.8 to 5.5.

11. The reconstituted solution of claim 10, comprising the anti SOST anti-sclerostin antibody at a concentration of 100 mg/ml, wherein the anti-sclerostin antibody comprises a light chain having the amino acid sequence of SEQ ID NO: 25, and a heavy chain having the amino acid sequence of SEQ ID NO: 22; the acetic acid-sodium acetate buffer at a concentration of 10 mM, trehalose at a concentration of 80 mg/ml, polysorbate 80 at a concentration of 0.4 mg/ml, and a calcium salt at a concentration of 4.5 mM, wherein the reconstituted solution has a pH of 4.8 to 5.5.

12. A kit comprising a container and the pharmaceutical composition of claim 1.

13. The pharmaceutical composition of claim 3, wherein the composition comprises the anti-sclerostin antibody.

14. The pharmaceutical composition of claim 5, wherein the composition comprises the anti-sclerostin antibody.

* * * * *

SEQUENCE LISTING

```
<160> NUMBER OF SEQ ID NOS: 25

<210> SEQ ID NO 1
<211> LENGTH: 117
<212> TYPE: PRT
<213> ORGANISM: murine

<400> SEQUENCE: 1

Glu Val Gln Leu Gln Gln Ser Gly Pro Glu Leu Val Lys Pro Gly Thr
1               5                   10                  15

Ser Val Lys Ile Pro Cys Gln Thr Ser Gly Tyr Thr Phe Thr Asp Tyr
            20                  25                  30

Asn Leu Asp Trp Leu Lys Gln Arg Pro Gly Glu Ser Leu Glu Trp Ile
        35                  40                  45

Gly Asp Ile Asp Pro Asn Asn Gly Asp Ile Leu Tyr Asn Gln Lys Phe
    50                  55                  60

Arg Asp Lys Ala Thr Leu Thr Val Asp Thr Ser Ser Asn Thr Ala Tyr
65                  70                  75                  80

Leu Glu Leu Arg Ser Leu Thr Ser Glu Asp Thr Ala Val Tyr Tyr Cys
                85                  90                  95

Ala Arg Arg Trp Ala Tyr Tyr Phe Asp Tyr Trp Gly Gln Gly Thr Thr
            100                 105                 110

Leu Thr Ile Ser Ser
        115

<210> SEQ ID NO 2
<211> LENGTH: 107
<212> TYPE: PRT
<213> ORGANISM: murine

<400> SEQUENCE: 2

Asn Ile Val Met Thr Gln Thr Pro Lys Leu Leu Phe Val Ser Ala Gly
1               5                   10                  15

Asp Arg Ile Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Thr Ser Asn Arg Phe Thr Gly Val Pro Asp Arg Phe Thr Gly
    50                  55                  60

Ser Gly Tyr Gly Thr Asp Phe Thr Leu Thr Ile Asn Thr Val Gln Ala
65                  70                  75                  80

Glu Asp Leu Ala Val Tyr Phe Cys Gln Gln Asp Tyr Ser Ser Pro Val
                85                  90                  95

Thr Phe Gly Ala Gly Thr Lys Leu Glu Leu Lys
            100                 105
```

```
<210> SEQ ID NO 3
<211> LENGTH: 5
<212> TYPE: PRT
<213> ORGANISM: murine

<400> SEQUENCE: 3

Asp Tyr Asn Leu Asp
1               5

<210> SEQ ID NO 4
<211> LENGTH: 17
<212> TYPE: PRT
<213> ORGANISM: murine

<400> SEQUENCE: 4

Asp Ile Asp Pro Asn Asn Gly Asp Ile Leu Tyr Asn Gln Lys Phe Arg
1               5                   10                  15

Asp

<210> SEQ ID NO 5
<211> LENGTH: 8
<212> TYPE: PRT
<213> ORGANISM: murine

<400> SEQUENCE: 5

Arg Trp Ala Tyr Tyr Phe Asp Tyr
1               5

<210> SEQ ID NO 6
<211> LENGTH: 11
<212> TYPE: PRT
<213> ORGANISM: murine

<400> SEQUENCE: 6

Lys Ala Ser Gln Ser Val Ser Asn Asp Val Ala
1               5                   10

<210> SEQ ID NO 7
<211> LENGTH: 7
<212> TYPE: PRT
<213> ORGANISM: murine

<400> SEQUENCE: 7

Tyr Thr Ser Asn Arg Phe Thr
1               5

<210> SEQ ID NO 8
<211> LENGTH: 9
<212> TYPE: PRT
<213> ORGANISM: murine

<400> SEQUENCE: 8

Gln Gln Asp Tyr Ser Ser Pro Val Thr
1               5

<210> SEQ ID NO 9
<211> LENGTH: 17
<212> TYPE: PRT
<213> ORGANISM: artificial sequence
<220> FEATURE:
<223> OTHER INFORMATION: Mutant HCDR2
```

<400> SEQUENCE: 9

Asp Ile Asp Pro Asn Asp Gly Asp Ile Leu Tyr Asn Gln Lys Phe Arg
1               5                   10                  15

Asp

<210> SEQ ID NO 10
<211> LENGTH: 117
<212> TYPE: PRT
<213> ORGANISM: artificial sequence
<220> FEATURE:
<223> OTHER INFORMATION: Ab-5 heavy chain variable region

<400> SEQUENCE: 10

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Leu Asp Trp Val Arg Gln Ala Pro Gly Gln Gly Leu Glu Trp Met
            35                  40                  45

Gly Asp Ile Asp Pro Asn Asn Gly Asp Ile Leu Tyr Asn Gln Lys Phe
        50                  55                  60

Arg Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Trp Ala Tyr Tyr Phe Asp Tyr Trp Gly Gln Gly Thr Thr
            100                 105                 110

Val Thr Val Ser Ser
        115

<210> SEQ ID NO 11
<211> LENGTH: 117
<212> TYPE: PRT
<213> ORGANISM: artificial sequence
<220> FEATURE:
<223> OTHER INFORMATION: Ab-9 heavy chain variable region

<400> SEQUENCE: 11

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Leu Asp Trp Leu Arg Gln Ala Pro Gly Glu Gly Leu Glu Trp Ile
            35                  40                  45

Gly Asp Ile Asp Pro Asn Asn Gly Asp Ile Leu Tyr Asn Gln Lys Phe
        50                  55                  60

Arg Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Trp Ala Tyr Tyr Phe Asp Tyr Trp Gly Gln Gly Thr Thr
            100                 105                 110

Val Thr Val Ser Ser
        115

<210> SEQ ID NO 12
<211> LENGTH: 117

```
<212> TYPE: PRT
<213> ORGANISM: artificial sequence
<220> FEATURE:
<223> OTHER INFORMATION: Ab-10 heavy chain variable region

<400> SEQUENCE: 12

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu Asp Trp Leu Arg Gln Ala Pro Gly Glu Gly Leu Glu Trp Ile
        35                  40                  45

Gly Asp Ile Asp Pro Asn Asp Gly Asp Ile Leu Tyr Asn Gln Lys Phe
    50                  55                  60

Arg Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Trp Ala Tyr Tyr Phe Asp Tyr Trp Gly Gln Gly Thr Thr
            100                 105                 110

Val Thr Val Ser Ser
            115

<210> SEQ ID NO 13
<211> LENGTH: 107
<212> TYPE: PRT
<213> ORGANISM: artificial sequence
<220> FEATURE:
<223> OTHER INFORMATION: Ab-5 light chain variable region

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Thr Ser Asn Arg Phe Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Val
                85                  90                  95

Thr Phe Gly Gly Gly Thr Lys Val Glu Ile Lys
            100                 105

<210> SEQ ID NO 14
<211> LENGTH: 107
<212> TYPE: PRT
<213> ORGANISM: artificial sequence
<220> FEATURE:
<223> OTHER INFORMATION: Ab-9 light chain variable region

<400> SEQUENCE: 14

Asn Ile Val Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30
```

Val Ala Trp Tyr Gln Gln Lys Pro Gly Lys Ser Pro Lys Leu Leu Ile
            35                  40                  45

Tyr Tyr Thr Ser Asn Arg Phe Thr Gly Val Pro Asp Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Asp Tyr Ser Ser Pro Val
                85                  90                  95

Thr Phe Gly Gly Gly Thr Lys Val Glu Ile Lys
            100                 105

<210> SEQ ID NO 15
<211> LENGTH: 107
<212> TYPE: PRT
<213> ORGANISM: artificial sequence
<220> FEATURE:
<223> OTHER INFORMATION: Ab-10 light chain variable region

<400> SEQUENCE: 15

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ser Pro Lys Leu Leu Ile
            35                  40                  45

Tyr Tyr Thr Ser Asn Arg Phe Thr Gly Val Pro Asp Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Asp Tyr Ser Ser Pro Val
                85                  90                  95

Thr Phe Gly Gly Gly Thr Lys Val Glu Ile Lys
            100                 105

<210> SEQ ID NO 16
<211> LENGTH: 326
<212> TYPE: PRT
<213> ORGANISM: Homo sapiens

<400> SEQUENCE: 16

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

```
Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 17
<211> LENGTH: 327
<212> TYPE: PRT
<213> ORGANISM: Homo sapiens

<400> SEQUENCE: 17

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

-continued

```
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 18
<211> LENGTH: 330
<212> TYPE: PRT
<213> ORGANISM: Homo sapiens

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
            210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 19
<211> LENGTH: 107
<212> TYPE: PRT
<213> ORGANISM: Homo sapiens

<400> SEQUENCE: 19

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 20
<211> LENGTH: 447
<212> TYPE: PRT
<213> ORGANISM: artificial sequence
<220> FEATURE:
<223> OTHER INFORMATION: humanized antibody Ab-10 heavy chain

<400> SEQUENCE: 20

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Asn Leu Asp Trp Val Arg Gln Ala Pro Gly Gln Gly Leu Glu Trp Met
        35                  40                  45
Gly Asp Ile Asp Pro Asn Asn Gly Asp Ile Leu Tyr Asn Gln Lys Phe
    50                  55                  60
Arg Asp Arg Val Thr Met Thr Thr Asp Thr Ser Thr Ser Thr Ala Tyr
65                  70                  75                  80
```

Met Glu Leu Arg Ser Leu Arg Ser Asp Asp Thr Ala Val Tyr Tyr Cys
                    85                  90                  95

Ala Arg Arg Trp Ala Tyr Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
    195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Asp Glu Leu Thr Lys Asn Gln Val Ser Leu Thr Cys Leu
    355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 21
<211> LENGTH: 444
<212> TYPE: PRT
<213> ORGANISM: artificial sequence
<220> FEATURE:
<223> OTHER INFORMATION: humanized antibody Ab-9 heavy chain

<400> SEQUENCE: 21

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu Asp Trp Leu Arg Gln Ala Pro Gly Glu Gly Leu Glu Trp Ile
        35                  40                  45

Gly Asp Ile Asp Pro Asn Asn Gly Asp Ile Leu Tyr Asn Gln Lys Phe
50                  55                  60

Arg Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Trp Ala Tyr Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

-continued

```
Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 22
<211> LENGTH: 443
<212> TYPE: PRT
<213> ORGANISM: artificial sequence
<220> FEATURE:
<223> OTHER INFORMATION: humanized antibody Ab-5 heavy chain

<400> SEQUENCE: 22

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu Asp Trp Leu Arg Gln Ala Pro Gly Glu Gly Leu Glu Trp Ile
        35                  40                  45

Gly Asp Ile Asp Pro Asn Asn Gly Asp Ile Leu Tyr Asn Gln Lys Phe
    50                  55                  60

Arg Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Trp Ala Tyr Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320
```

```
Ser Asn Lys Gly Leu Pro Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly
            435                 440
```

<210> SEQ ID NO 23
<211> LENGTH: 214
<212> TYPE: PRT
<213> ORGANISM: artificial sequence
<220> FEATURE:
<223> OTHER INFORMATION: humanized antibody Ab-10 light chain

<400> SEQUENCE: 23

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
                20                  25                  30

Val Ala Trp Tyr Gln Gln Lys Pro Gly Lys Ala Pro Lys Leu Leu Ile
            35                  40                  45

Tyr Tyr Thr Ser Asn Arg Phe Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Val
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 24

```
<211> LENGTH: 214
<212> TYPE: PRT
<213> ORGANISM: artificial sequence
<220> FEATURE:
<223> OTHER INFORMATION: humanized antibody Ab-9 light chain

<400> SEQUENCE: 24

Asn Ile Val Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ser Pro Lys Leu Leu Ile
        35                  40                  45

Tyr Tyr Thr Ser Asn Arg Phe Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Asp Tyr Ser Ser Pro Val
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 214
<212> TYPE: PRT
<213> ORGANISM: artificial sequence
<220> FEATURE:
<223> OTHER INFORMATION: humanized antibody Ab-5 light chain

<400> SEQUENCE: 25

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ser Pro Lys Leu Leu Ile
        35                  40                  45

Tyr Tyr Thr Ser Asn Arg Phe Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Asp Tyr Ser Ser Pro Val
                85                  90                  95
```

```
Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```